US012343271B2

(12) United States Patent
Higgins

(10) Patent No.: US 12,343,271 B2
(45) Date of Patent: Jul. 1, 2025

(54) LOADING TOOLS FOR PROSTHETIC VALVE DEVICES

(71) Applicant: Medtronic, Inc., Minneapolis, MN (US)

(72) Inventor: Craig Higgins, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 618 days.

(21) Appl. No.: 17/701,906

(22) Filed: Mar. 23, 2022

(65) Prior Publication Data

US 2022/0346991 A1 Nov. 3, 2022

Related U.S. Application Data

(60) Provisional application No. 63/183,172, filed on May 3, 2021.

(51) Int. Cl.
*A61F 2/95* (2013.01)
*A61F 2/24* (2006.01)

(52) U.S. Cl.
CPC .......... *A61F 2/9522* (2020.05); *A61F 2/2427* (2013.01)

(58) Field of Classification Search
CPC .... A61F 2/9522; A61F 2/2427; A61F 2/9525; A61F 2/2418; A61F 2/011; A61F 2/2481
See application file for complete search history.

(56) References Cited

U.S. PATENT DOCUMENTS

| 6,167,605 | B1 | 1/2001 | Morales |
| 8,359,721 | B2 | 1/2013 | Melsheimer et al. |
| 9,192,469 | B2 | 11/2015 | Mearns et al. |
| 9,414,914 | B2 | 8/2016 | Duffy et al. |
| 2011/0208296 | A1 | 8/2011 | Duffy et al. |
| 2015/0081011 | A1 | 3/2015 | Young et al. |
| 2018/0280174 | A1 | 10/2018 | Dwork |
| 2019/0053900 | A1 | 2/2019 | Finn et al. |

FOREIGN PATENT DOCUMENTS

WO 20201358430 A1 7/2020

OTHER PUBLICATIONS

Written Opinion issued Jul. 26, 2022 in Intl Appl. No. PCT/IB2022/054027.

*Primary Examiner* — Jerrah Edwards
*Assistant Examiner* — Hanna L Pasqualini

(57) ABSTRACT

A loading tool to facilitate loading a prosthesis into a delivery system includes a hinged body with first and second body portions and a collar slidingly disposed over the hinged body. First ends of the body portions are attached and second ends of the body portions are not attached. Each body portion includes a resilient clip that includes a radial protrusion. Each resilient clip is configured to displaced radially inwards when a pinching force is applied thereto. The loading tool has an open configuration in which the second ends are radially spaced apart and the collar is disposed over the first ends. The loading tool has a closed configuration in which the second ends are disposed directly adjacent to each other and the collar is disposed over the second ends. The radial protrusions lock the loading tool in the closed configuration when the resilient clips are not displaced radially inwards.

20 Claims, 13 Drawing Sheets

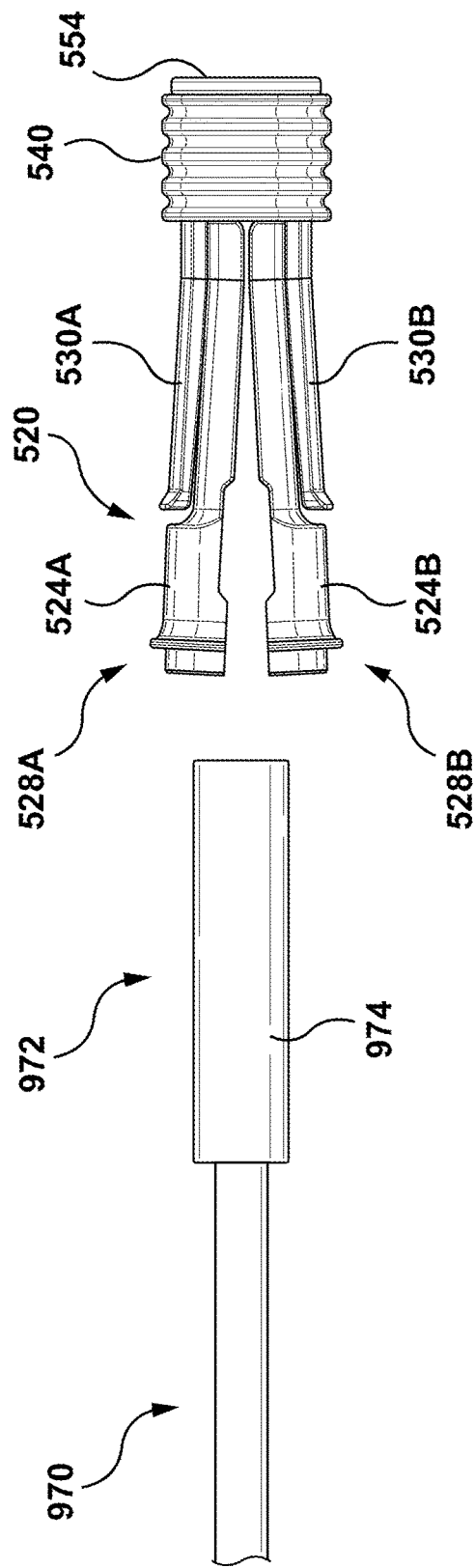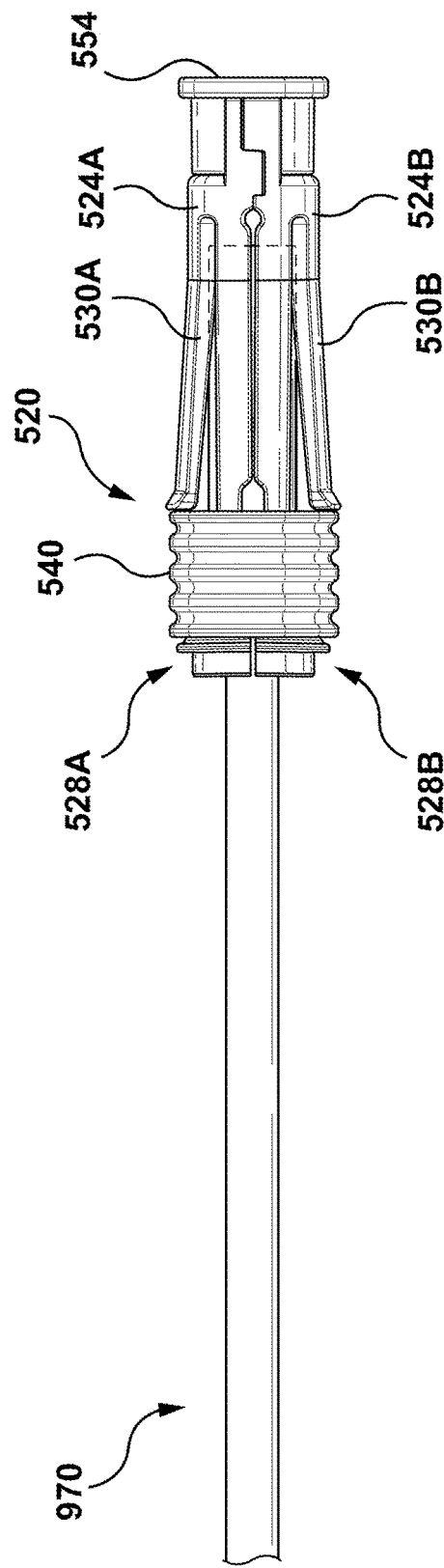
FIG. 9
FIG. 10

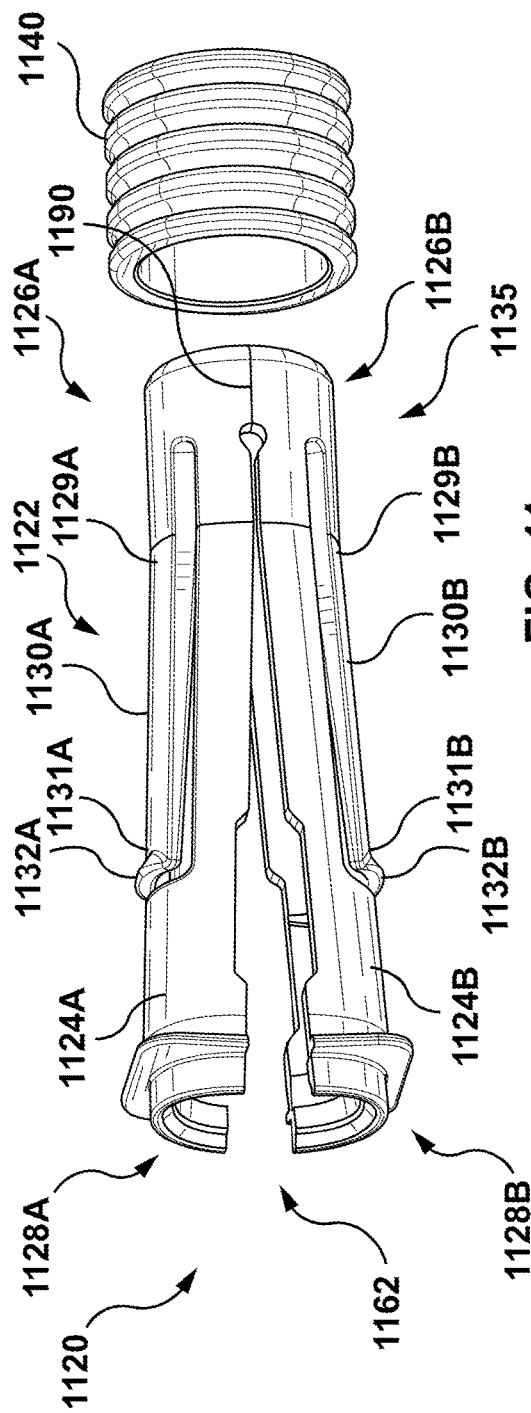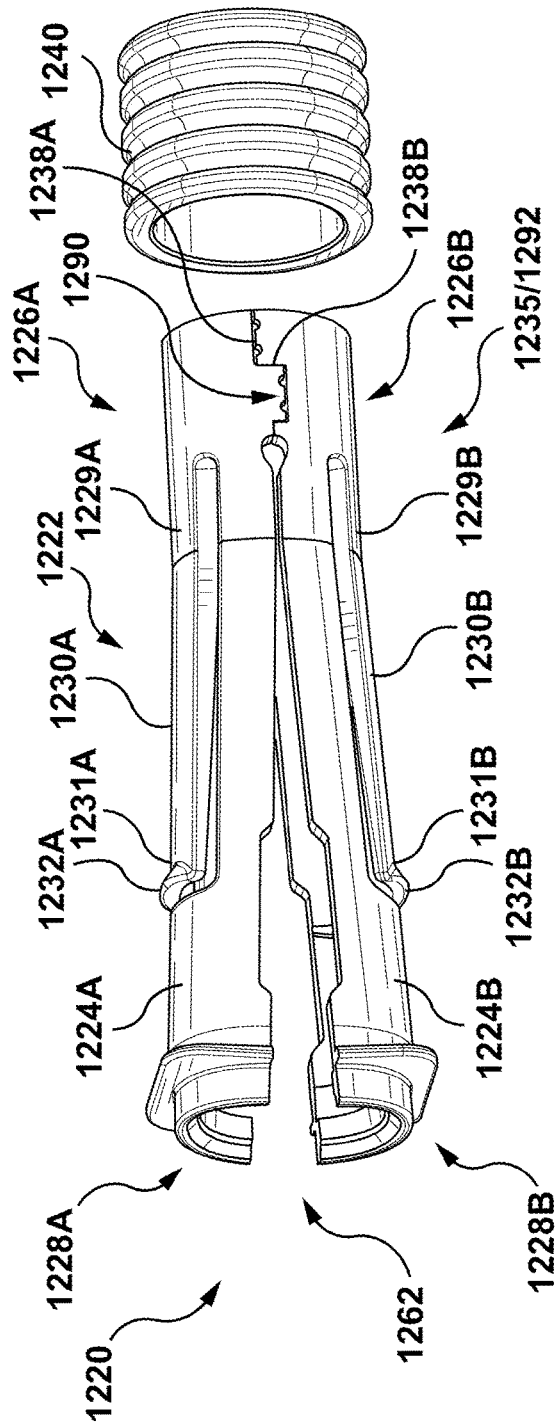
FIG. 11
FIG. 12

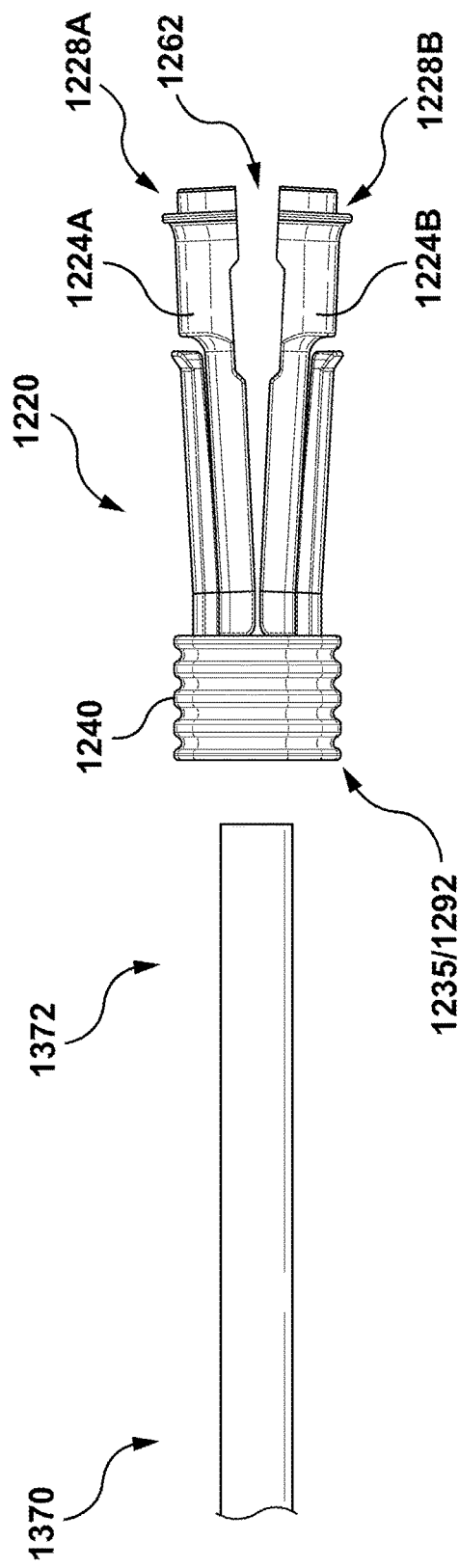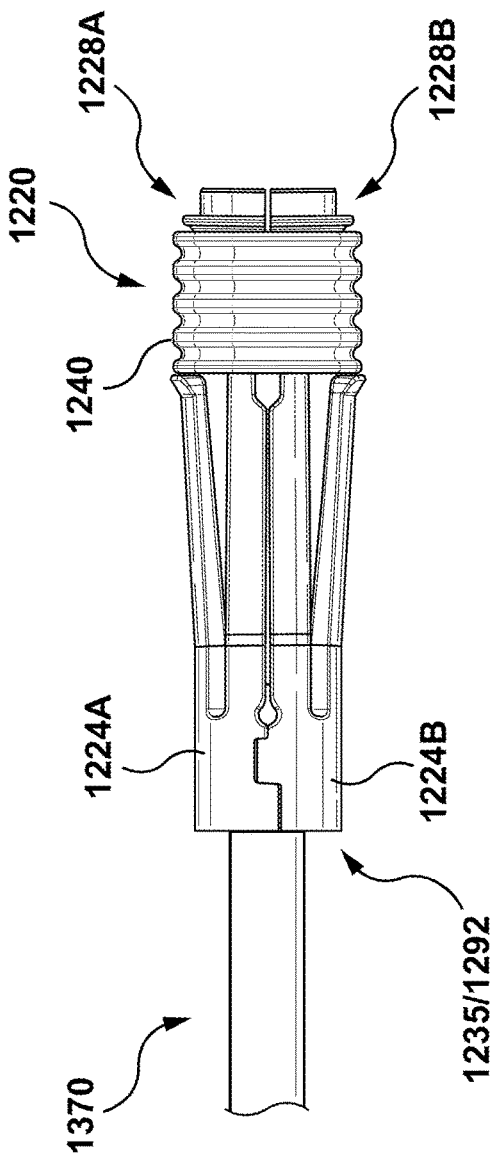
FIG. 13
FIG. 14

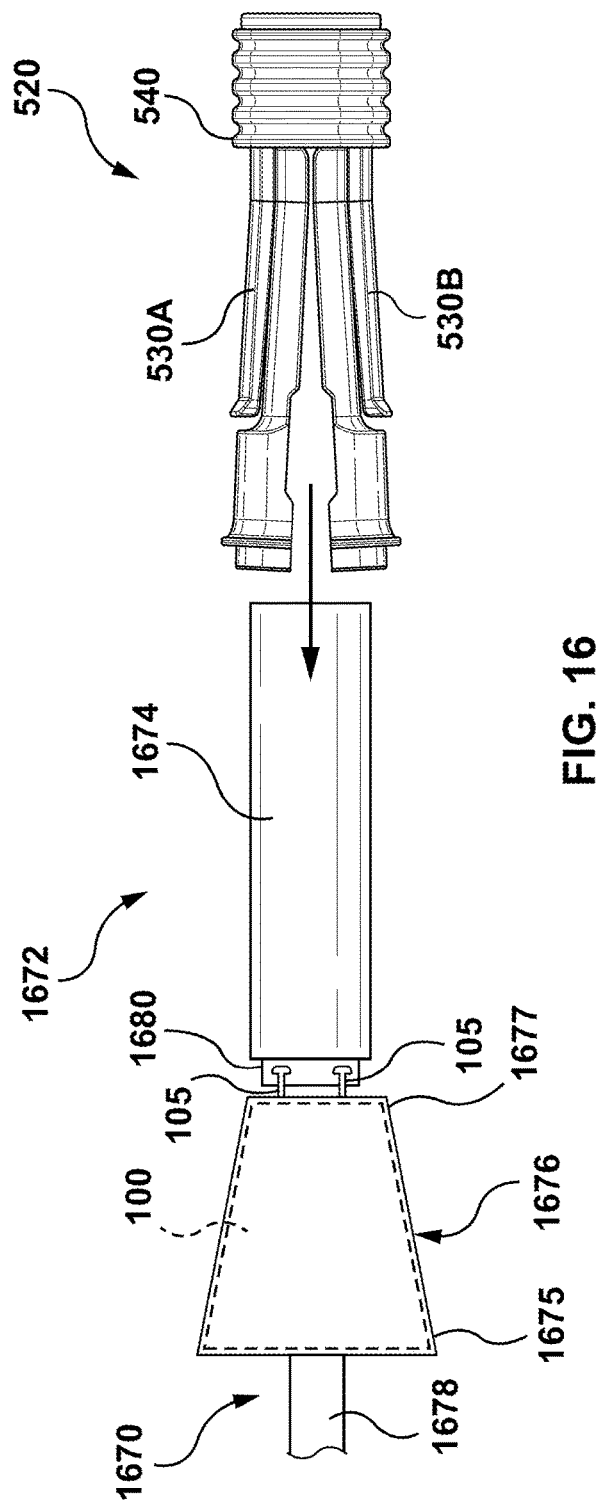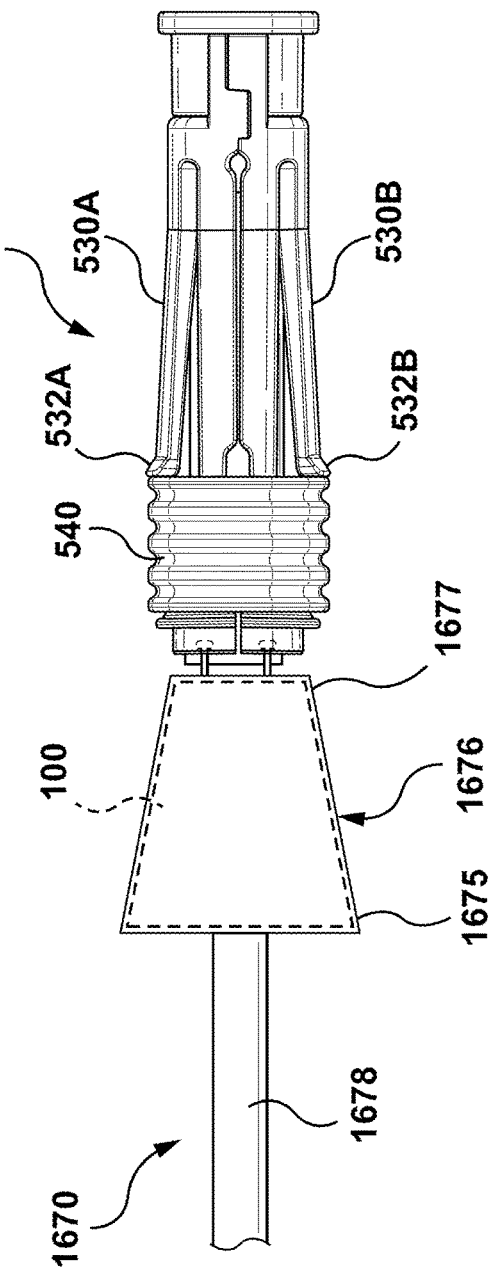

LOADING TOOLS FOR PROSTHETIC VALVE DEVICES

CROSS-REFERENCE TO RELATED APPLICATIONS

This application claims the benefit of U.S. Provisional Application No. 63/183,172, filed May 3, 2021, which is hereby incorporated by reference in its entirety for all purposes.

FIELD

The present technology is related to self-expanding prosthetic valve devices, and in particular is directed to tools that facilitate loading prosthetic valve devices into a delivery system.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses are delivered in a radially compressed or crimped configuration so that the heart valve prosthesis can be advanced through the patient's vasculature. Once positioned at the treatment site, the heart valve prosthesis is expanded to engage tissue at the diseased heart valve region to, for instance, hold the heart valve prosthesis in position.

The present disclosure relates to tools to facilitate loading or crimping of a heart valve prosthesis as well as other types of protheses into a catheter-based delivery system.

SUMMARY

According to a first embodiment hereof, the present disclosure provides a loading tool to facilitate loading a self-expanding prosthesis into a delivery system. The loading tool includes a hinged body and a collar slidingly disposed over the hinged body. The hinged body includes a first body portion and a second body portion, each of the first body portion and the second body portion having a first end and a second end. The first end of the first body portion is attached to the first end of the second body and the second end of the first body portion is not attached to the second end of the second body portion. Each of the first body portion and the second body portion includes a resilient clip formed thereon that includes a radial protrusion on an outer surface thereof. Each resilient clip is configured to displaced radially inwards when a pinching force is applied thereto. The loading tool has an open configuration in which the second end of the first body portion and the second end of the second body portion are radially spaced apart from each other and the collar is disposed over the first ends of the first and second body portions. The loading tool has a closed configuration in which the second end of the first body portion and the second end of the second body portion are disposed directly adjacent to each other and the collar is disposed over the second ends of the first and second body portions. The radial protrusions are configured to lock the loading tool in the closed configuration when the resilient clips are not displaced radially inwards.

In an aspect of the first embodiment, and in combination with any other aspects herein, the disclosure provides that each of the first body portion and the second body portion has a flange on an outer surface thereof at the second end thereof and the collar is sandwiched between the flanges and the radial protrusions on the resilient clips when the collar locks the hinged body in the closed configuration.

In an aspect of the first embodiment, and in combination with any other aspects herein, the disclosure provides that each flange has a square profile.

In an aspect of the first embodiment, and in combination with any other aspects herein, the disclosure provides that each radial protrusion has a tapered outer surface that permits the collar to slide in a direction from the first ends of the first and second body portions towards the second ends of the first and second body portions and each radial protrusion has an end surface that does not permit the collar to slide in a direction from the second ends of the first and second body portions towards the first ends of the first and second body portions unless the resilient clips are displaced radially inwards by the pinching force.

In an aspect of the first embodiment, and in combination with any other aspects herein, the disclosure provides that the first end of the first body portion is attached to the first end of the second body via adhesive.

In an aspect of the first embodiment, and in combination with any other aspects herein, the disclosure provides that the first end of the first body portion is attached to the first end of the second body via a mechanical fastener.

In an aspect of the first embodiment, and in combination with any other aspects herein, the disclosure provides that the loading tool is prevented from opening when the radial protrusions lock the loading tool in the closed configuration.

In an aspect of the first embodiment, and in combination with any other aspects herein, the disclosure provides the resilient clips are configured to be displaced radially inwards to release the collar.

In an aspect of the first embodiment, and in combination with any other aspects herein, the disclosure provides that the hinged body is configured to be disposed over a distal end of the delivery system during loading of the self-expanding prosthesis into the delivery system.

In an aspect of the first embodiment, and in combination with any other aspects herein, the disclosure provides that the hinged body is configured to be disposed over a capsule of the delivery system when the self-expanding prosthesis is positioned into the capsule.

In an aspect of the first embodiment, and in combination with any other aspects herein, the disclosure provides that the second ends of the first and second body portions each include a stepped edge formed on an inner surface thereof configured to prevent the self-expanding prosthesis from contacting a first end of the capsule when the self-expanding prosthesis is positioned into the capsule and configured to retain attachment bars of the self-expanding prosthesis.

In an aspect of the first embodiment, and in combination with any other aspects herein, the disclosure provides that the first and second body portions collectively have a tubular configuration when the loading tool is in the closed configuration.

According to a first embodiment hereof, the present disclosure provides a method of loading a self-expanding prosthesis into a delivery system includes placing a loading tool in an open configuration. The loading tool includes a hinged body and a collar slidingly disposed over the hinged body. The hinged body includes a first body portion and a second body portion, each of the first body portion and the second body portion having a first end and a second end. The first end of the first body portion is attached to the first end of the second body and the second end of the first body portion is not attached to the second end of the second body portion. Each of the first body portion and the second body portion includes a resilient clip formed thereon that includes a radial protrusion on an outer surface thereof. Each resilient clip is configured to displaced radially inwards when a pinching force is applied thereto. The loading tool has an open configuration in which the second end of the first body portion and the second end of the second body portion are radially spaced apart from each other and the collar is disposed over the first ends of the first and second body portions. The loading tool is disposed in the open configuration over a distal end of the delivery system and while the loading tool is disposed over a distal end of the delivery system, the collar is slid over the hinged body until the loading tool is in a closed configuration. In the closed configuration the second end of the first body portion and the second end of the second body portion are disposed directly adjacent to each other and the collar is disposed over the second ends of the first and second body portions, and wherein the radial protrusions lock the loading tool in the closed configuration when the resilient clips are not displaced radially inwards. The self-expanding prosthesis is loaded into the distal end of the delivery system while the radial protrusions lock the loading tool in the closed configuration.

In an aspect of the second embodiment, and in combination with any other aspects herein, the disclosure provides that after the self-expanding prosthesis is loaded into the distal end of the delivery system, a pinching force is applied to displace the resilient clips radially inward. The collar is slid over the hinged body while the resilient clips are displaced radially inward until the loading tool is in the open configuration and the loading tool is removed from the distal end of the delivery system.

In an aspect of the second embodiment, and in combination with any other aspects herein, the disclosure provides that the self-expanding prosthesis is a mitral valve prosthesis.

In an aspect of the second embodiment, and in combination with any other aspects herein, the disclosure provides that each of the first body portion and the second body portion has a flange on an outer surface thereof at the second end thereof and the collar is sandwiched between the flanges and the radial protrusions on the resilient clips when the collar locks the hinged body in the closed configuration.

In an aspect of the second embodiment, and in combination with any other aspects herein, the disclosure provides that each flange has a square profile and the flange sets against a flat surface during the step of loading the self-expanding prosthesis.

In an aspect of the second embodiment, and in combination with any other aspects herein, the disclosure provides that each radial protrusion has a tapered outer surface that permits the collar to slide in a direction from the first ends of the first and second body portions towards the second ends of the first and second body portions and wherein each radial protrusion has an end surface that does not permit the collar to slide in a direction from the second ends of the first and second body portions towards the first ends of the first and second body portions unless the resilient clips are displaced radially inwards by the pinching force.

In an aspect of the second embodiment, and in combination with any other aspects herein, the disclosure provides that the loading tool is prevented from opening to the open configuration when the radial protrusions lock the loading tool in the closed configuration.

In an aspect of the second embodiment, and in combination with any other aspects herein, the disclosure provides that the distal end of the delivery system is a capsule.

In an aspect of the second embodiment, and in combination with any other aspects herein, the disclosure provides that the second ends of the first and second body portions each include a stepped edge formed on an inner surface thereof configured to prevent the self-expanding prosthesis from contacting a first end of the capsule when the self-expanding prosthesis is positioned into the capsule and configured to retain attachment bars of the self-expanding prosthesis.

In an aspect of the second embodiment, and in combination with any other aspects herein, the disclosure provides that the first and second body portions collectively have a tubular configuration when the loading tool is in the closed configuration.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 9 depicts a side view of the loading tool of FIG. 5 prior to positioning over a distal end of a delivery system, wherein the delivery system is configured for transfemoral delivery and wherein the loading tool is in the open configuration.

FIG. 10 depicts a side view of the loading tool of FIG. 5 after positioning over the distal end of the delivery system, wherein the loading tool is in the closed configuration.

FIG. 11 depicts an exploded view of a loading tool in accordance with another aspect of the disclosure, wherein first and second body portions of the loading tool are attached to each other via adhesive and the loading tool is open at only one end thereof.

FIG. 12 depicts an exploded view of a loading tool in accordance with another aspect of the disclosure, wherein first and second body portions of the loading tool are attached to each other via adhesive and the loading tool is open at both ends thereof.

FIG. 13 depicts a side view of the loading tool of FIG. 12 prior to positioning over a distal end of a delivery system, wherein the delivery system is configured for transapical delivery and wherein the loading tool is in the open configuration.

FIG. 14 depicts a side view of the loading tool of FIG. 12 after positioning over the distal end of the delivery system, wherein the delivery system is configured for transapical delivery and wherein the loading tool is in the closed configuration.

FIG. 16 depicts a side view of the loading tool of FIG. 5 prior to positioning over a distal end of a delivery system, wherein the delivery system is configured for transfemoral delivery and wherein the loading tool is in the open configuration, and wherein a loading funnel is disposed over the delivery system.

FIG. 17 depicts a side view of the loading tool of FIG. 5 after positioning over the distal end of the delivery system, wherein the loading tool is in the closed configuration.

DETAILED DESCRIPTION

Figure 1:
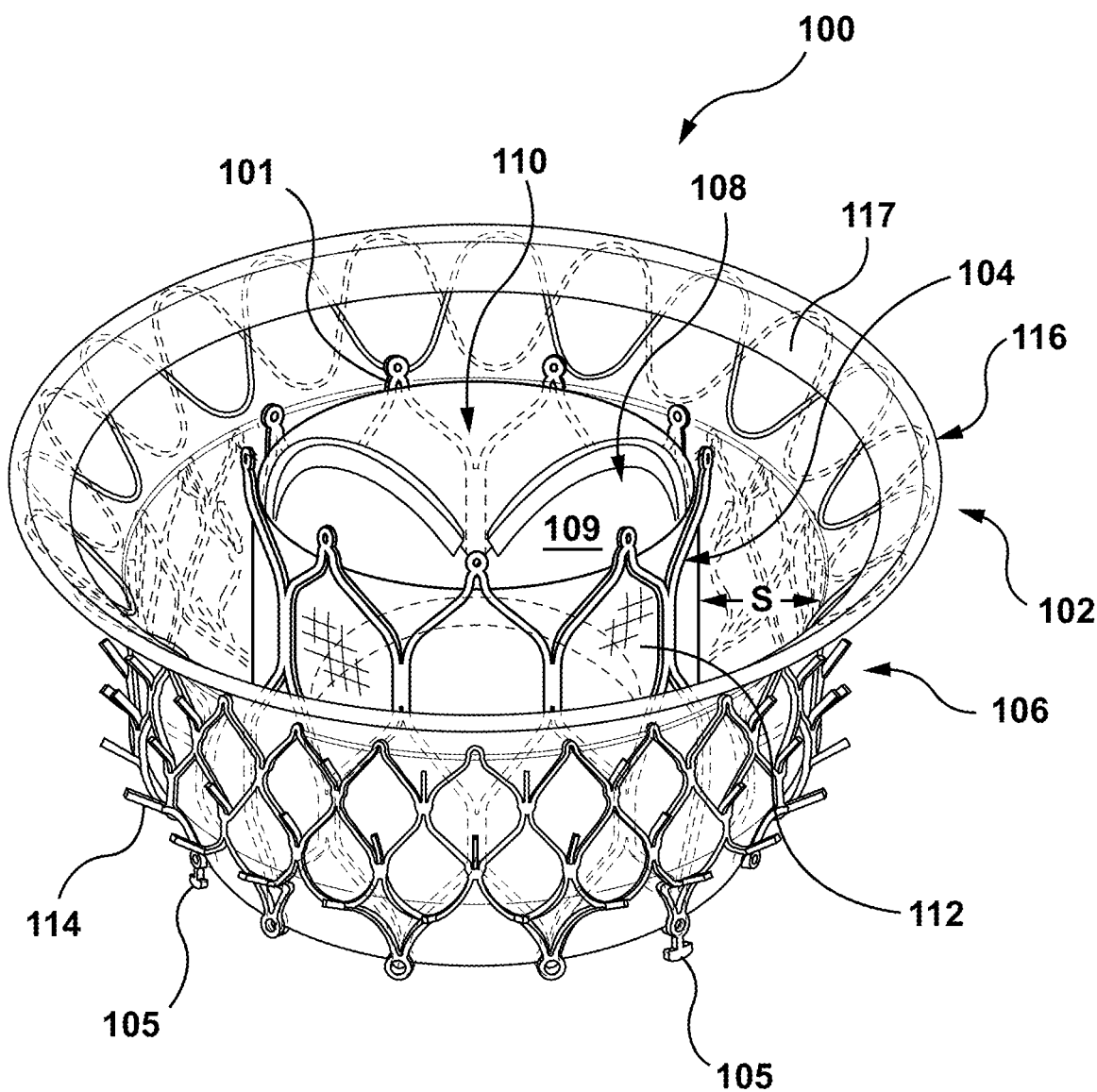
FIG. 1 depicts a perspective view of an exemplary transcatheter valve prosthesis for use with a loading tool in accordance with an aspect of the disclosure.

Specific embodiments of the present invention are now described with reference to the figures, wherein like reference numbers indicate identical or functionally similar elements. Unless otherwise indicated, the terms "distal" and "proximal", when used in the following description to refer to a sheath, a delivery device, or a catheter-based delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the treating clinician.

Embodiments of the present invention relate to loading tools to facilitate loading a self-expanding prosthesis into a delivery system. A loading tool according to embodiments hereof is configured to be disposed over a distal end of a delivery system while a self-expanding prosthesis is positioned or pulled into the distal end of the delivery system. The loading tool according to embodiments hereof is configured to prevent damage to the self-expanding prosthesis during loading thereof into the delivery system, as will be explained in more detail herein. In addition, the loading tool includes integral resilient clips that are configured to automatically lock a slidable collar of the loading tool into place once it reaches a predetermined position. When the slidable collar is locked into position, the resilient clips provide a robust hard mechanical stop and the loading tool is likewise locked in a closed configuration such that the loading tool is prevented from opening. The slidable collar may be unlocked only when a user pinches or radially compresses the resilient clips to thereby release the slidable collar. When locked, the loading tool can withstand high radial loading forces, including loading forces equal to or greater than 370 N. In an embodiment, the loading tool can withstand radial loading forces greater than 370 N. As such, the loading tool may be utilized with self-expanding prostheses that have a high radial loading force such as but not limited to transcatheter valve prostheses which are configured for implantation within a native mitral valve. Further, the loading tool is easy to operate by the user and is also provided to the user as a single unit such that assembly by the user is not required.

FIGS. 1-4 illustrate a transcatheter valve prosthesis 100 that may be utilized with embodiments of loading tools described herein. The heart valve prosthesis 100 is illustrated herein in order to facilitate description of the present invention. The following description of the transcatheter valve prosthesis 100 is merely exemplary in nature and is not intended to limit the invention or the application and uses of the invention. It is understood that any number of alternate heart valve prostheses can be used with the loading tools described herein. Other non-limiting examples of transcatheter heart valve prostheses that can be used with the loading tools described herein are described in U.S. application Ser. No. 16/853,851 to McVeigh et al., U.S. Pat. No. 9,034,032 to McLean et al. and International Patent Application No. PCT/US2014/029549 to McLean et al, U.S. Patent Application Publication No. 2012/0101572 to Kovalsky et al., U.S. Patent Application Publication No. 2012/0035722 to Tuval, U.S. patent application Publication No. 2006/0265056 to Nguyen et al., U.S. Patent Application Publication No. 2007/05409266 to Birdsall, and U.S. patent application Publication No. 2007/05409269 to Dolan et al., each of which is incorporated by reference herein in its entirety. Although the transcatheter valve prosthesis 100 is a heart valve prosthesis configured for placement within a mitral heart valve, embodiments of loading tools described herein may be utilized when loading any self-expanding transcatheter valve prostheses into a delivery system. For example, embodiments of loading tools described herein may be utilized with a transcatheter heart valve configured for placement within a pulmonary, aortic, mitral, or tricuspid valve, or may be utilized with a transcatheter valve prosthesis configured for placement within a venous valve or within other body passageways where it is deemed useful. There is no intention to be bound by any expressed or implied theory presented in the preceding technical field, background, brief summary or the following detailed description. In addition, embodiments of loading members described herein may be utilized when loading any self-expanding prostheses into a delivery system, and it is not required that the self-expanding prosthesis include a prosthetic valve component disposed therein.

A perspective view of the transcatheter valve prosthesis 100 in accordance with an aspect of the disclosure is shown in FIG. 1. The transcatheter valve prosthesis 100 is configured to be radially compressed into a reduced-diameter crimped configuration for delivery within a vasculature (not shown) and to return to an expanded, deployed configuration, as shown in FIG. 1. Stated another way, the transcatheter valve prosthesis 100 has a crimped configuration for delivery within a vasculature and an expanded configuration for deployment within a native heart valve. In accordance with embodiments hereof, when in the crimped configuration, the transcatheter valve prosthesis 100 has a low profile suitable for delivery to and deployment within a native heart valve via a suitable delivery catheter that may be tracked to the deployment site of the native heart valve of a heart via any one of a transseptal, retrograde, or transapical approach. The transcatheter valve prosthesis 100 includes a stent or frame 102 and a prosthetic valve component 108 including at least one leaflet disposed within and secured to the frame 102.

Any portion of the frame 102 described herein as an element of a heart valve prosthesis 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material would be selected to provide the transcatheter heart valve prosthesis 100 to be configured to be compressed into a reduced-diameter crimped configuration for transcatheter delivery to a native valve, whereby release from a delivery catheter returns the prosthesis to an expanded, deployed configuration.

In an aspect of the disclosure, the frame 102 of the transcatheter valve prosthesis 100 includes a valve support 104 at least partially surrounded by and coupled to an anchor element 106. The valve support 104 is a tubular stent-like or frame structure that defines a central lumen 110 from an inflow end 101 of the valve support 104 to an outflow end 103 of the valve support 104. The valve support 104 is configured to support the prosthetic valve component 108 therein, which will be described in more detail below. In an embodiment, the valve support 104 has a substantially cylindrical shape in which the outflow end 103 of the valve support 104 has a diameter that is substantially the same as a diameter of the inflow end 101 of the valve support 104.

The valve support 104 includes a skirt 112 coupled to a surface thereof. More particularly, the skirt 112 is coupled to an inner surface of the valve support 104 to line a portion thereof. Alternatively, the skirt 112 may be coupled to an outer surface of the valve support 104 to enclose a portion thereof as would be known to one of ordinary skill in the art of prosthetic valve construction. The skirt 112 may be a natural or biological material such as pericardium or another membranous tissue such as intestinal submucosa. Alternatively, the skirt 112 may be a low-porosity woven fabric, such as polyester, Dacron fabric, or PTFE, which creates a one-way fluid passage when attached to the stent. In one embodiment, the skirt 112 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

In an aspect of the disclosure, the anchor element 106 is a stent-like or frame structure that functions as an anchor for the transcatheter valve prosthesis 100 to secure its deployed position within a native annulus. The anchor element 106 is a substantially cylindrically-shaped structure that is configured to engage heart tissue at or below an annulus of a native heart valve, such as an annulus of a native mitral valve. At the inflow end 101 of the valve support 104, the anchor element 106 is radially spaced a distance S from the valve support 104 to mechanically isolate the inflow end 101 of the valve support 104 from the anchor element 106. The anchor element 106 includes one or more cleats or prongs 114 that extend outward from an exterior side thereof to engage heart tissue. In another embodiment, the anchor element 106 may employ barbs, spikes, or other tissue fixation mechanisms for engaging heart tissue.

The transcatheter valve prosthesis 100 further includes a brim or rim element 116 that extends outwardly from an upstream end of the anchor element 106. The brim element 116 includes overlapping, 180 degree out of phase sinusoidal wire forms that are attached and hinged to the anchor element 106 by a suitable biocompatible low-profile fabric 117 used in bioprosthetic implants namely endovascular grafts, heart valves or left atrial appendage devices to promote bio-integration, such as woven polyethylene terephthalate (PET) fabric. The brim element 116 may act as an atrial retainer, if present, and to serve such a function the brim element 116 may be configured to engage tissue above a native annulus, such as a supra-annular surface or some other tissue in the left atrium, to thereby inhibit downstream migration of a prosthetic heart valve 100, for e.g., during atrial systole.

Figure 2:
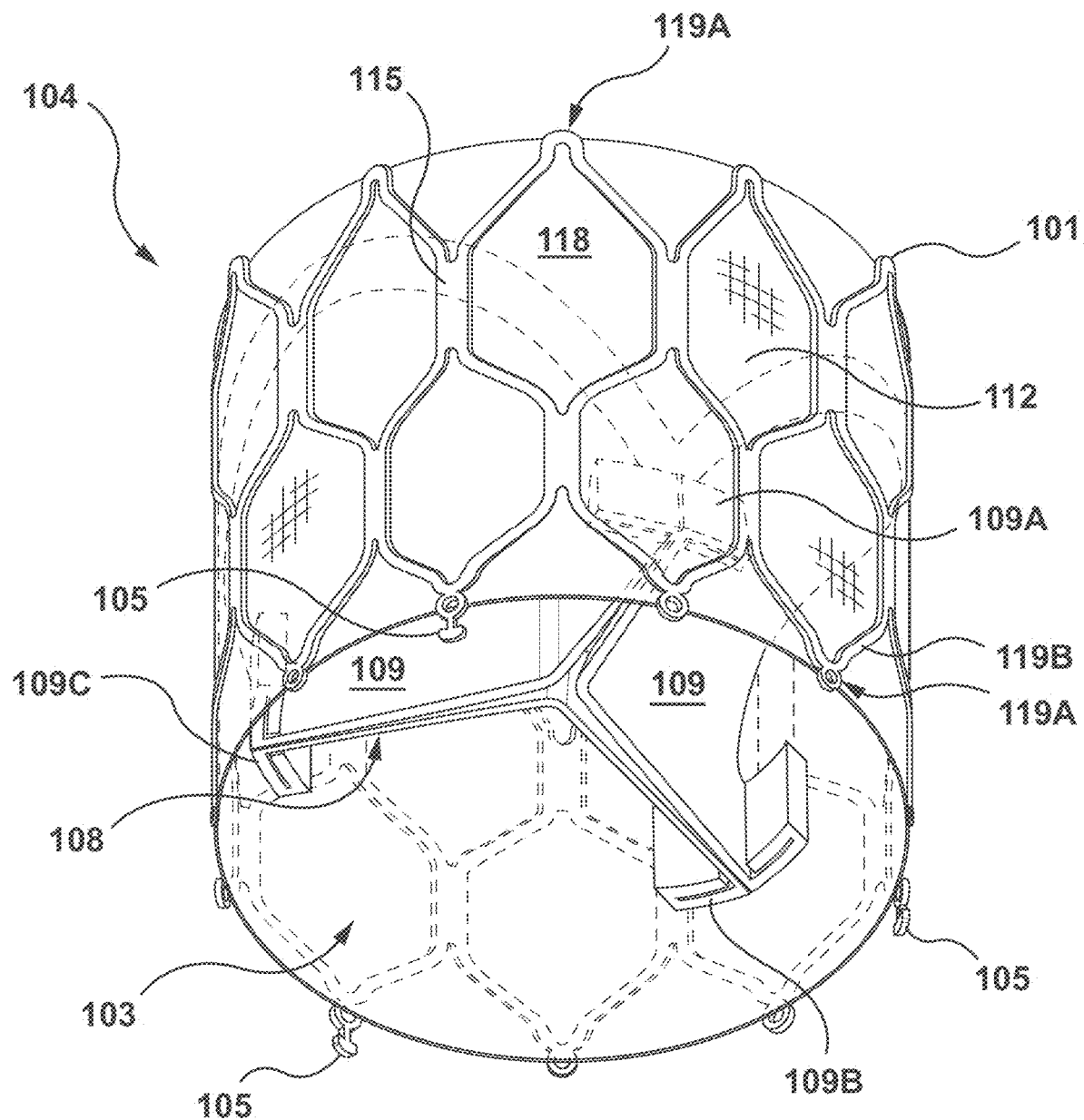
FIG. 2 depicts a perspective view of a valve support of the transcatheter valve prosthesis of FIG. 1 with a prosthetic valve component secured therein in accordance with an aspect of the disclosure.

Referring to FIG. 2, the structure of the valve support 104 will now be described in more detail. The valve support 104 includes a plurality of crowns 119A and a plurality of struts 119B with each crown 119A being formed between a pair of opposing struts 119B. Each crown 119A is a curved segment or bend extending between opposing struts 119B. The valve support 104 is tubular, with the plurality of side openings 118 being defined by edges of the plurality of crowns 119A and the plurality of struts 119B. In an embodiment, the plurality of side openings 118 may be substantially diamond-shaped. The valve support 104 includes a plurality of nodes 115. A node 115 is defined as a region where two crowns of the plurality of crowns 119A within the valve support 104 meet or connect. The skirt 112 is attached to an inner surface of the valve support 104 around a circumference thereof. The skirt 112 lines the inner surface of the valve support 104. At the inflow end 101 thereof, the valve support 104 includes a plurality of attachment bars 105 extending therefrom that function to releasably couple the transcatheter valve prosthesis 100 to a delivery system.

Figure 4:
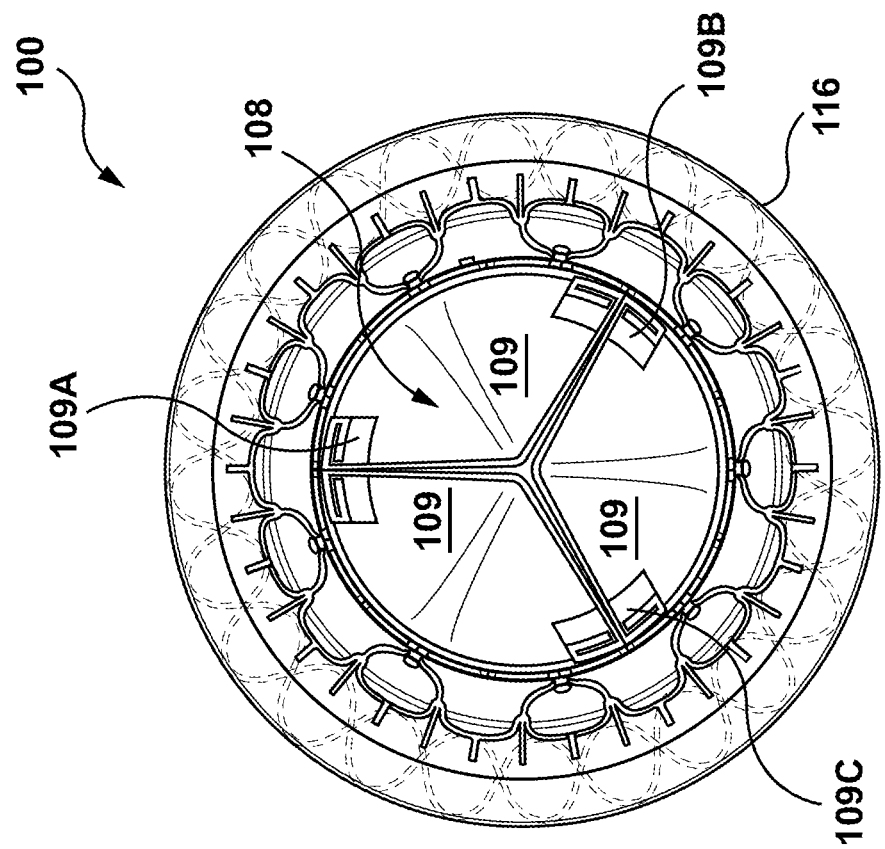
FIG. 4 depicts a ventricular end view of the transcatheter valve prosthesis shown in FIG. 1 in accordance with an aspect of the disclosure.
Figure 3:
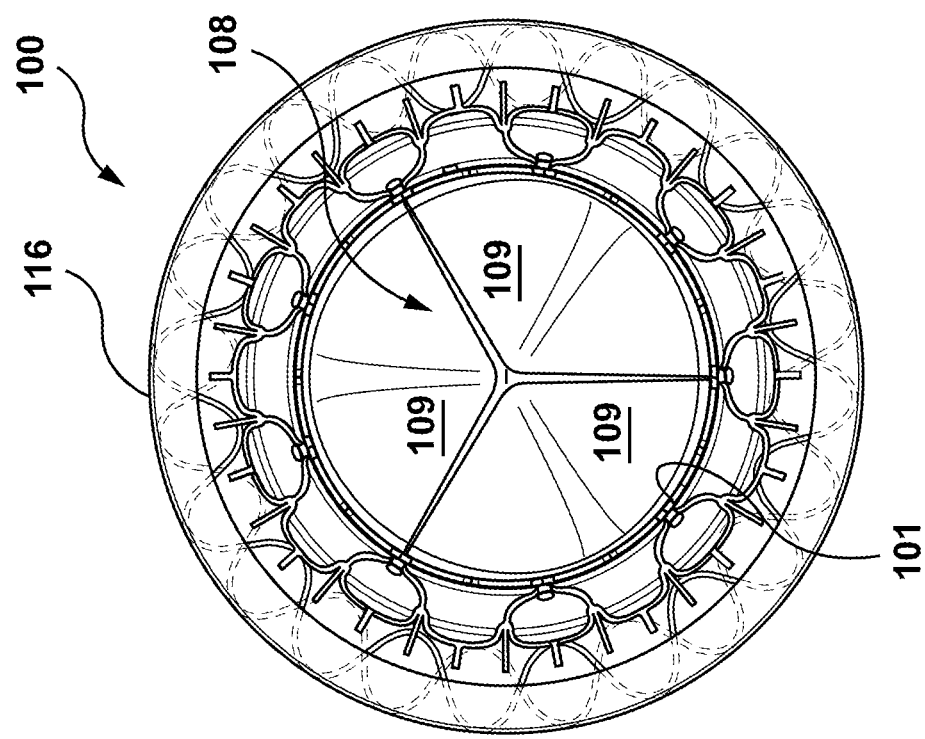
FIG. 3 depicts an atrial end view of the transcatheter valve prosthesis shown in FIG. 1 in accordance with an aspect of the disclosure.

The prosthetic valve component 108 of the transcatheter valve prosthesis 100 is capable of regulating flow therethrough via valve leaflets that may form a replacement valve. FIGS. 1-4 illustrate an exemplary prosthetic valve component having three leaflets, although a single leaflet or bicuspid leaflet configuration may alternatively be used in embodiments hereof. When deployed in situ, the prosthetic valve component 108 in a closed state is configured to block blood flow in one direction to regulate blood flow through the central lumen 110 of the valve support 104. FIG. 2 depicts a perspective view of the valve support 104 with a prosthetic valve component 108 secured therein, the valve support 104 being shown in FIG. 2 removed from the remainder of the transcatheter valve prosthesis 100 shown in FIG. 1 for ease of illustration. FIG. 3 depicts an atrial or inflow end view of the transcatheter valve prosthesis 100 shown in FIG. 1, and FIG. 4 depicts a ventricular or outflow end view of the transcatheter valve prosthesis 100 shown in FIG. 1. The prosthetic valve component 108 includes valve leaflets 109, e.g., three valve leaflets 109, that are disposed to coapt within an upstream portion of the valve support 104 with leaflet commissures 109A, 109B, 109C of the valve leaflets 109 being secured within a downstream portion of the valve support 104, such that the valve leaflets 109 open during diastole. Leaflets 109 are attached along their bases to the valve support 104, for example, using sutures or a suitable biocompatible adhesive. Adjoining pairs of leaflets 109 are attached to one another at their lateral ends to form leaflet commissures 109A, 109B, 109C. The orientation of the leaflets 109 within the valve support 104 depends upon on which end of the transcatheter valve prosthesis 100 is the inflow end and which end of the transcatheter valve prosthesis 100 is the outflow end, thereby ensuring one-way flow of blood through the transcatheter valve prosthesis 100.

The valve leaflets 109 may be attached to the skirt 112. The valve leaflets 109 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

For delivery, the transcatheter valve prosthesis 100 is radially compressed into a reduced-diameter crimped configuration onto a delivery system for delivery within a vasculature. As known in the art, the delivery system includes an inner shaft that receives the transcatheter valve prosthesis 100 on a distal portion thereof and an outer sheath or capsule that is configured to compressively retain the transcatheter valve prosthesis 100 on the distal portion of the inner shaft during delivery. Stated another way, the outer sheath or capsule surrounds and constrains the transcatheter valve prosthesis 100 in the radially compressed or crimped configuration. An exemplary delivery system for delivering the transcatheter valve prosthesis 100 is described in U.S. Pat. No. 9,034,032 to McLean et al. and International Patent Application No. PCT/US2014/029549 to McLean et al, previously incorporated by reference herein. However, it will be apparent to one of ordinary skill in the art that other delivery systems may be utilized and that the components of the delivery system may vary depending upon the configuration and structure of the transcatheter valve prosthesis that is being delivered.

As stated above, embodiments of the present invention relate to a loading tool to facilitate loading the transcatheter valve prosthesis 100 into a delivery system. The loading tool is disposed over a distal end of the delivery system while the transcatheter valve prosthesis 100 is retracted or pulled into the distal end of the delivery system. For sake of illustration, use of the loading tool is described herein with respect to the transcatheter valve prosthesis 100, as the structure of the transcatheter valve prosthesis 100 has already been described in detail above. However, as previously stated, the loading tools described herein may be utilized when loading any self-expanding prosthesis into a delivery system, and it is not required that the self-expanding prosthesis include a prosthetic valve component disposed therein.

Figure 5:
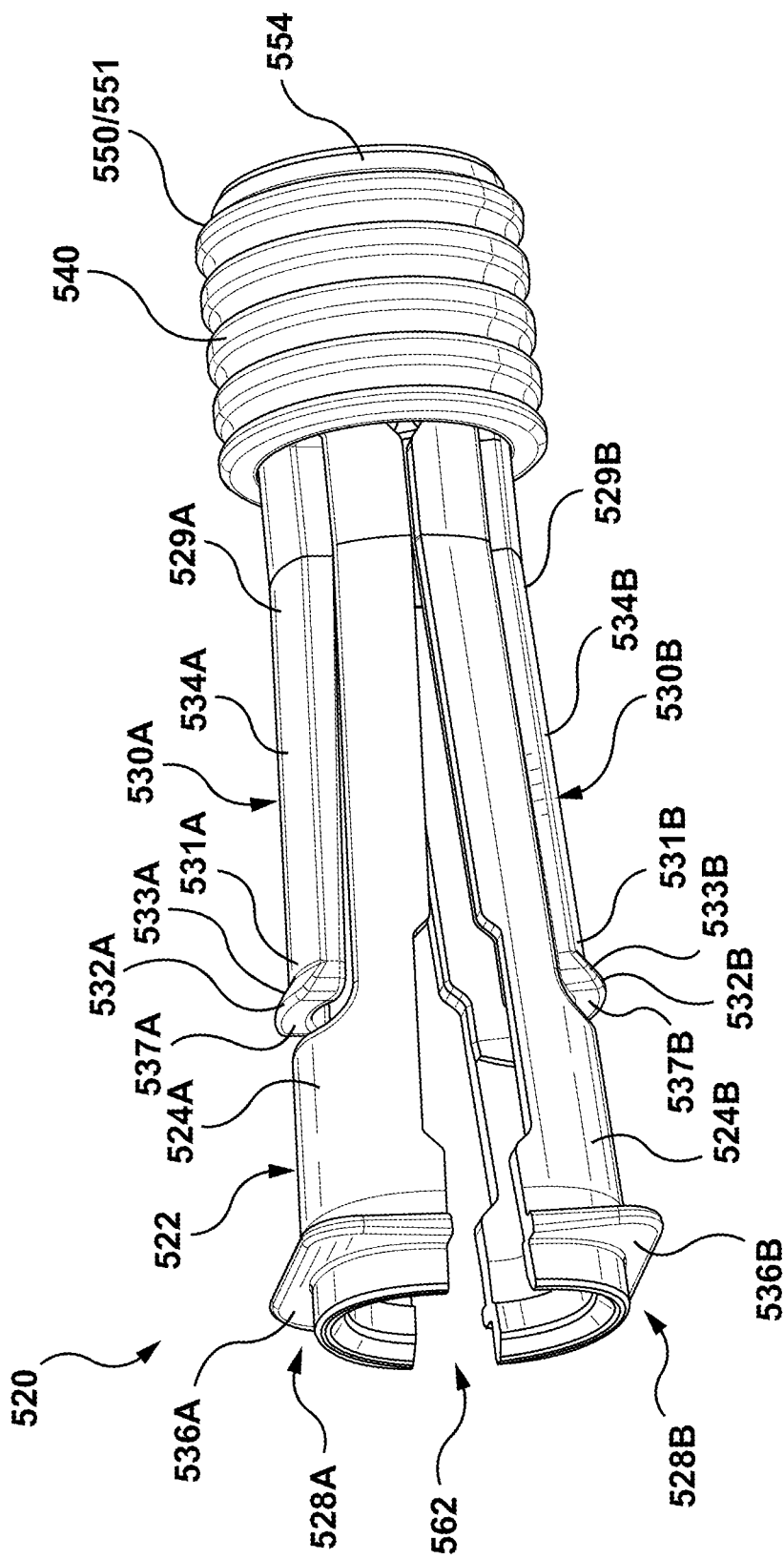
FIG. 5 depicts a perspective view of a loading tool in accordance with an aspect of the disclosure, wherein the loading tool is in an open configuration.
Figure 6:
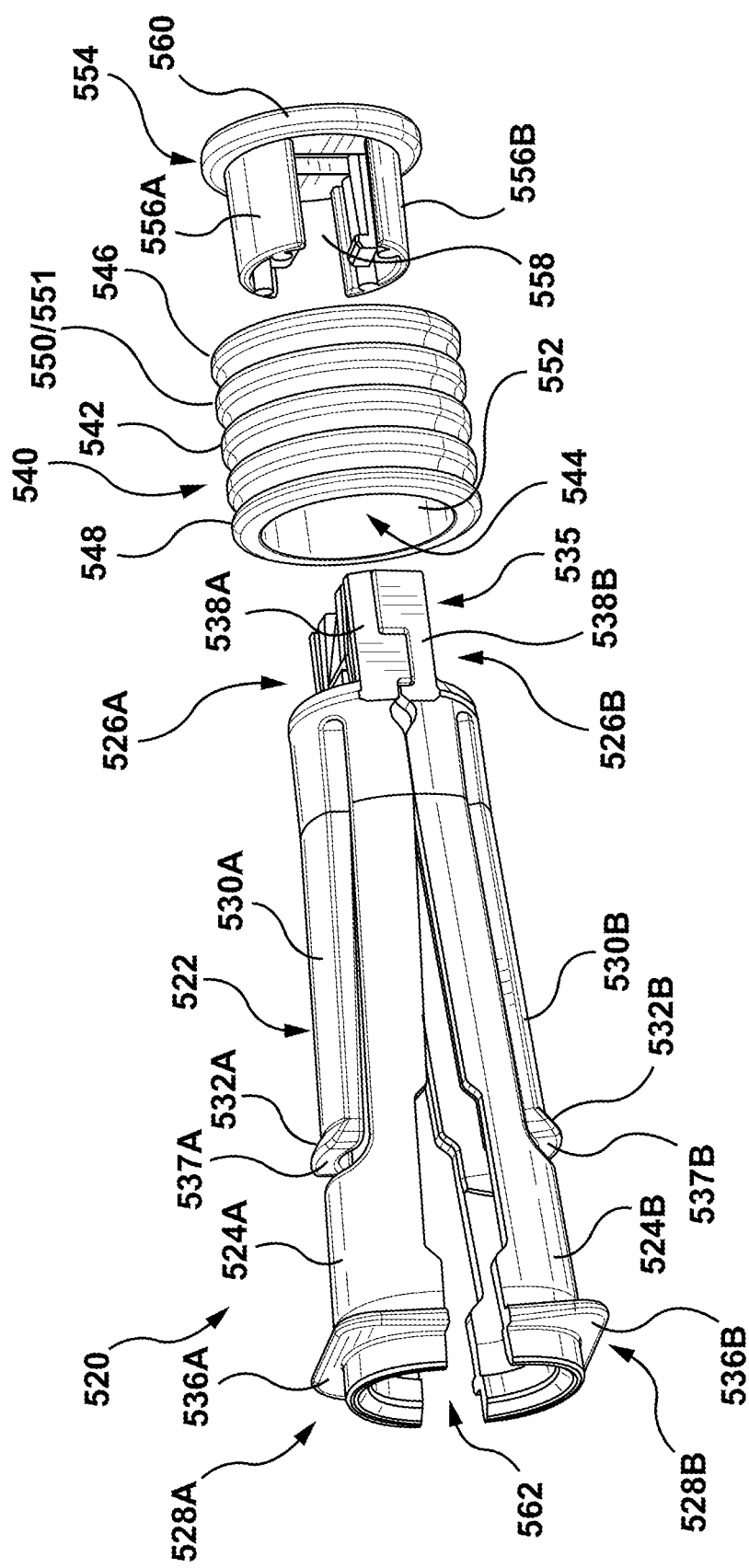
FIG. 6 depicts an exploded view of the loading tool of FIG. 5.

More particularly, a loading tool 520 is depicted in FIGS. 5-8B. FIG. 5 depicts a perspective view of the loading tool 520, while FIG. 6 depicts an exploded view of the loading tool 520 for illustrative purposes. The loading tool 520 includes a hinged body 522, a collar 540 slidingly disposed over the hinged body 522, and a fastener 554. The hinged body 522 includes a first body half or portion 524A and a second body half or portion 524B. The first and second body portions 524A, 524B collectively define the hinged body 522, which is configured to dynamically open and close mechanically via sliding movement of the collar 540 as will be described in more detail herein. The hinged body 522 is sized or configured to be disposed over a distal end of the delivery system during loading of the transcatheter valve prosthesis 100 into a delivery system, as described in more detail with respect to FIGS. 9 and 10.

Each of the first body portion 524A and the second body portion 524B has a first end 526A, 526B and a second end 528A, 528B, respectively. The first end 526A of the first body portion 524A is attached to the first end 526B of the second body 524B via the fastener 554 and the second end 528A of the first body portion 524A is not attached to the second end 528B of the second body portion 524B. The attached first ends 526A, 526B form a hinged end 535 of the loading tool 520. The attached first ends 526A, 526B may include interlocking or mating surfaces 538A, 538B as best shown on the exploded view of FIG. 6.

Each of the first body portion 524A and the second body portion 524B includes a resilient clip 530A, 530B integrally formed thereon that includes a radial protrusion 532A, 532B on an outer surface 534A, 534B thereof, respectively. Each resilient clip 530A, 530B is a flap or tab formed on its respective body portion such that it is configured to be displaced radially inwards when a pinching force is applied thereto. Each resilient clip 530A, 530B includes a first end 529A, 529B that is attached to or extends from the respective body portion 524A, 524B and a second end 531A, 531B that is detached from the respective body portion 524A, 524B. The radial protrusions 532A, 532B are formed on the second ends 531A, 531B of the resilient clips 530A, 530B. Each resilient clip 530A, 530B has a thickness that tapers along a length thereof in the direction from the first end 529A, 529B thereof to the second end 531A, 531B thereof. More particularly, as best shown on FIG. 8B, each resilient clip 530A, 530B has a first thickness $T_1$ at the first end 529A, 529B thereof which is greater than a second thickness $T_2$ at the second end 531A, 531B thereof. The thickness of each resilient clip 530A, 530B may continuously or gradually taper between the first thickness $T_1$ to the second thickness $T_2$. The tapering thicknesses of the resilient clips 530A, 530B provide or result in sufficient clearance for the resilient clips 530A, 530B to be displaced radially inwards when a pinching force is applied thereto and thereby allow the collar 540 to slidingly advance over the radial protrusions 532A, 532B, as will be described in more detail herein.

The collar 540 has a tubular body 542 with a first end 546 and a second or opposing end 548, and the tubular body 542 defines a lumen or passageway 544 therethrough such that the tubular body 542 may be slidingly disposed over the hinged body 522. An outer surface 550 of the collar 540 includes a plurality of ribs 551 so that the collar 540 may be easily gripped by a user for sliding motion of the collar 540 along the hinged body. An inner surface 552 of the collar 540 is sized or configured to be only slightly larger than the outer surface of the hinged body 522 so that the collar 540 may be easily moved back and forth along the hinged body 522, and so that the collar 540 forces the second ends 528A, 528B of the first and second body portions 524A, 524B together when disposed thereover as will be described in more detail herein.

The fastener 554 includes a disk 560 that is flat, round, and configured to close an end of the hinged body 522 when assembled to the first and second body portions 524A, 524B. The fastener 554 also includes two opposing fingers 556A, 556B extending axially from the disk 560. Each finger 556A, 556B has a rounded or arc cross-section along its length and the fingers 556A, 556B are spaced apart from each other by a transverse opening 558. The transverse opening 558 is sized or configured to receive the first ends 526A, 526B of the first and second body portions 524A, 524B, and the fingers 556A, 556B are configured to mechanically couple to the first ends 526A, 526B of the first and second body portions 524A, 524B. The fastener 554 thus attaches or fastens the first and second body portions 524A, 524B together. The fastener 544 also contains the collar 540 so that the collar 540 cannot slide off the hinged body 522. Particularly, the disk 560 has an outer diameter that is slightly greater than the outer diameter of the collar 540 so that when the collar 540 is disposed over the hinged body 522, the collar 540 cannot slide over the disk 560 of the fastener 554. Stated another way, the disk 560 of the fastener 554 functions as a stopper for the collar 540. The loading tool 520 is thus provided to the user as a single, assembled tool that does not require any assembly by the user.

Adjacent to the second ends 528A, 528B of the first and second body portions 524A, 524B, each body portion includes a fin or flange 536A, 536B extending radially outward from the outer surface thereof. In an embodiment, each flange 536A, 536B has a square profile so that the loading tool 520 is configured to rest upon a flat surface, i.e., a tabletop, without rolling. Similar to the fastener 544 adjacent to the first ends 526A, 526B of the first and second body portions 524A, 524B, the flanges 536A, 536B also function to contain the collar 540 so that the collar 540 cannot slide off the hinged body 522 adjacent to the second ends 528A, 528B of the first and second body portions 524A, 524B. Particularly, collectively the flanges 536A, 536B have an outer diameter that is slightly greater than the outer diameter of the collar 540 so that when the collar 540 is disposed over the hinged body 522, the collar 540 cannot slide over the flanges 536A, 536B. Stated another way, the flanges 536A, 536B function as a stopper for the collar 540.

Figure 7:
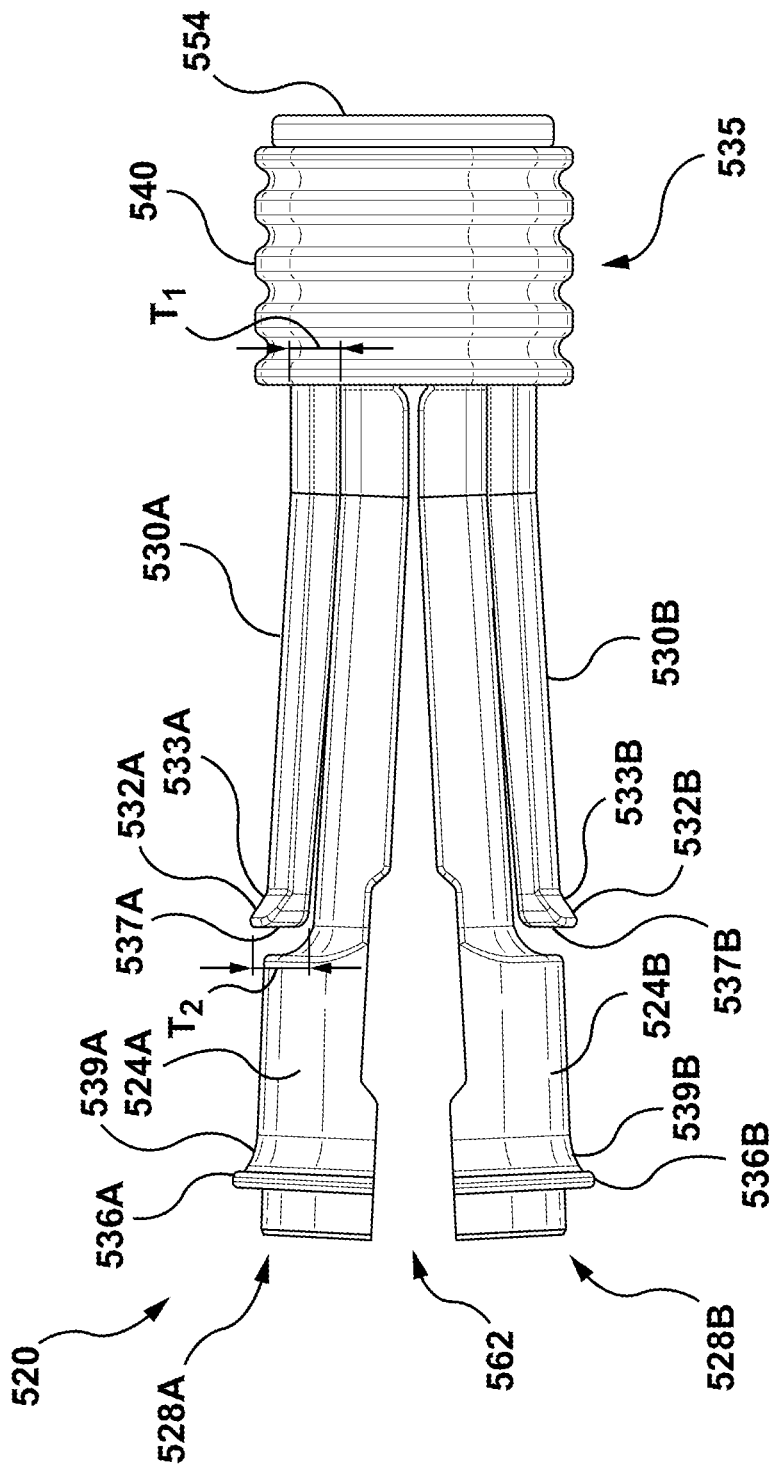
FIG. 7 depicts a side view of the loading tool of FIG. 5, wherein the loading tool is in the open configuration.

The loading tool 520 is initially formed or shape set in an open configuration in which the second end 528A of the first body portion 524A and the second end 528B of the second body portion 524B are radially spaced apart from each other as shown in FIG. 5 and the side view of FIG. 7. Further, when in the open configuration, the collar 540 is disposed over the first ends 526A, 526B of the first and second body portions 524A, 524B. The open configuration provides the loading tool 520 with a splayed opening 562 at an end thereof which allows the loading tool 520 to easily slide over the delivery system during the loading process, and further to easily slide off the delivery system after the loading process is complete.

Figure 8A:
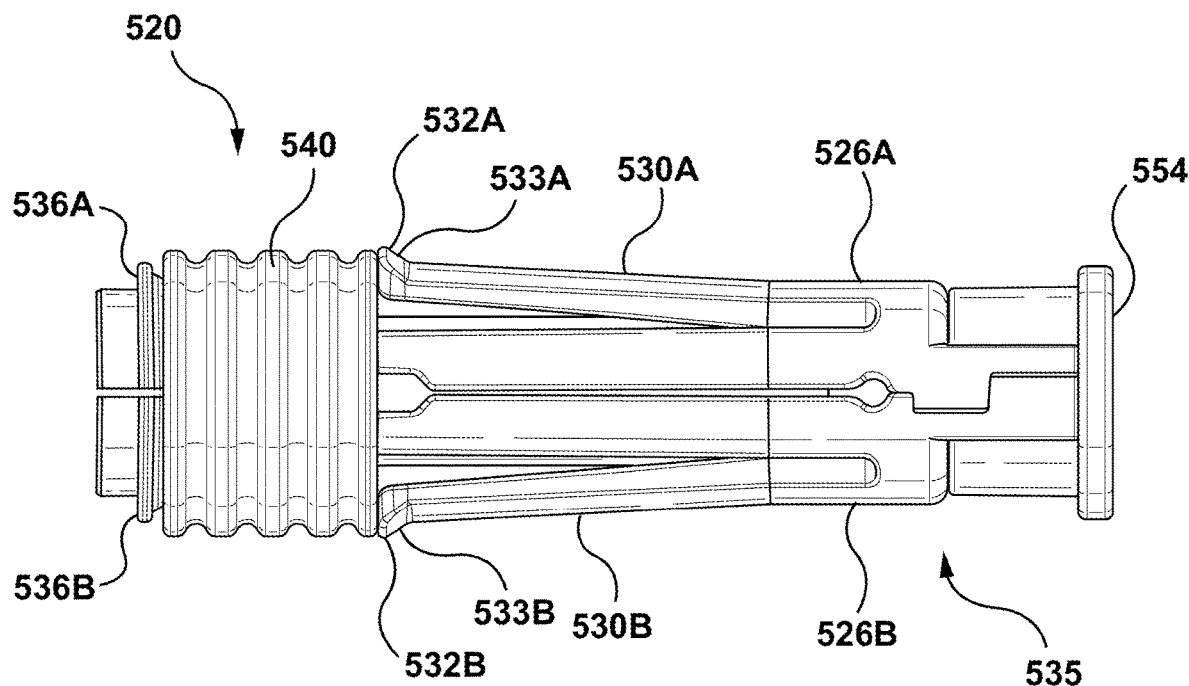
FIG. 8A depicts a side view of the loading tool of FIG. 5, wherein the loading tool is in a closed configuration.
Figure 8B:
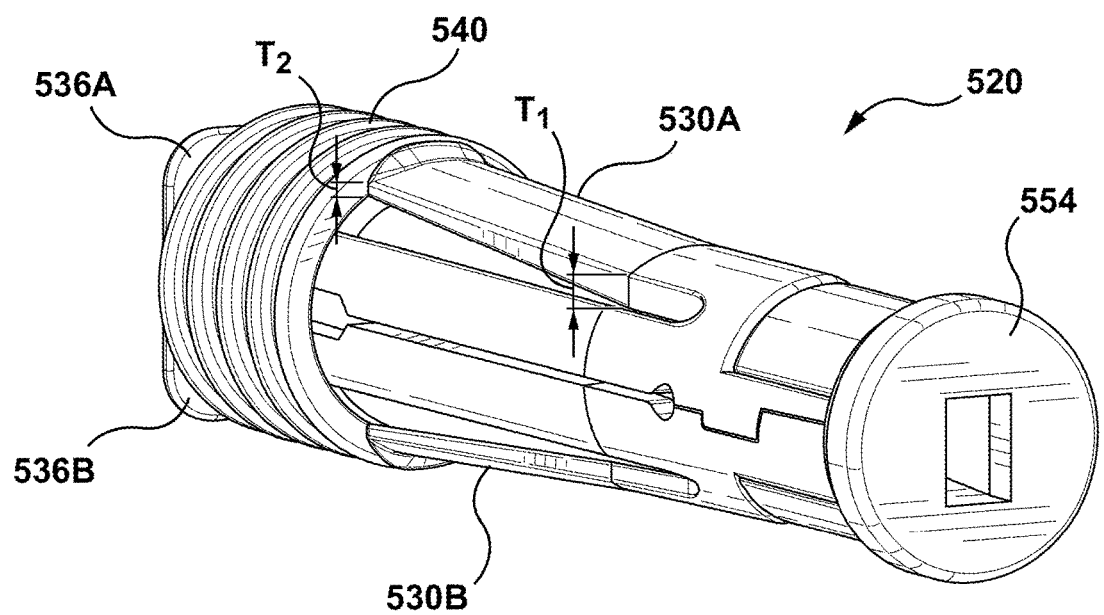
FIG. 8B depicts a perspective view of the loading tool of FIG. 5, wherein the loading tool is in the closed configuration.

FIGS. 8A and 8B depict side and perspective views of the loading collar 520 in a closed configuration in which the second end 528A of the first body portion 524A and the second end 528B of the second body portion 524B are disposed directly adjacent to each other and the collar 540 is disposed over the second ends 528A, 528B of the first and second body portions 524A, 524B. As used herein with respect to the closed configuration of loading collars described herein, "disposed directly adjacent to each other" includes the second end 528A of the first body portion 524A and the second end 528B of the second body portion 524B contacting or abutting against each other, as well as the second end 528A of the first body portion 524A and the second end 528B of the second body portion 524B being disposed relative to each other with a small nominal, predetermined radial gap therebetween with no intervening structures therebetween. When in the closed configuration, the second end 528A of the first body portion 524A and the second end 528B of the second body portion 524B are disposed radially closer to each other relative to the open configuration thereof. When in the closed configuration, the radial protrusions 532A, 532B of the resilient clips 530A, 530B are configured to abut against the collar 540 to lock the loading tool 520 in the closed configuration. Thus, the collar 540 is sandwiched between the radial protrusions 532A, 532B of the resilient clips 530A, 530B and the flanges 536A, 536B when the collar 540 locks the hinged body 522 in the closed configuration. Each of the first and second body portions 524A, 524B further include a tapered outer surface 539A, 539B, respectively, (which is best shown on FIG. 7) adjacent to the flanges 536A, 536B which ensure a tight interference fit when the collar 540 is sandwiched between the radial protrusions 532A, 532B of the resilient clips 530A, 530B and the flanges 536A, 536B. The loading tool 520 is prevented from opening when the radial protrusions 532A, 532B lock the collar 540 and the loading tool 520 in the closed configuration so that the loading tool 540 will not slip or pop open until the loading procedure is complete. Being locked in the closed configuration ensures that the transcatheter valve prosthesis 100 is protected from mis-load related damage during loading.

Each radial protrusion 532A, 532B has a tapered outer surface 533A, 533B that permits the collar 540 to slide in a direction from the first ends 526A, 526B of the first and second body portions 524A, 524B towards the second ends 528A, 528B of the first and second body portions 524A, 524B. Stated another way, when the user moves the collar 540 in a direction from the first ends 526A, 526B of the first and second body portions 524A, 524B towards the second ends 528A, 528B of the first and second body portions 524A, 524B, the collar 540 traverses the radial protrusions 532A, 532B via the tapered outer surfaces 533A, 533B without any additional user intervention. As the collar 540 traverses the radial protrusions 532A, 532B, the resilient clips 530A, 530B may be displaced radially inwards by the collar 540. However, after the collar 540 traverses the radial protrusions 532A, 532B, the resilient clips 530A, 530B spring or revert back to their formed or shape set position once the collar 540 is no longer disposed thereover. When the resilient clips 530A, 530B spring or revert back to their formed or shape set position, a tactile click is felt by the user to provide feedback that the loading tool 520 is locked in the closed configuration.

Each radial protrusion 532A, 532B has an end surface 537A, 537B that does not permit the collar 540 to slide in a direction from the second ends 528A, 528B of the first and second body portions 524A, 524B towards the first ends 526A, 526B of the first and second body portions 524A, 524B unless the resilient clips 530A, 530B are displaced radially inwards by a user. When in the closed configuration, the end surfaces 537A, 537B of the radial protrusions 532A, 532B are configured to abut against the collar 540 and thereby provide a hard mechanical stop for the collar 540, which also provides the user with visual feedback that the loading tool 520 is locked in the closed configuration.

When it is desired to unlock the loading tool 520 for removal thereof, i.e., after the loading procedure is complete, the user moves or radially displaces the resilient clips 530A, 530B inwards to release the collar 540. Stated another way, when the user pinches the resilient clips 530A, 530B, the collar 540 may traverse the radial protrusions 532A, 532B since the end surfaces 537A, 537B of the radial protrusions 532A, 532B are displaced radially inwards. Thus, when the resilient clips 530A, 530B are displaced inwards by the user, the user may retract the collar 540 to revert the loading tool 520 back to its open configuration. When in the open configuration, the loading tool 520 may be easily removed from the delivery system.

The set-up of the loading tool 520 onto a delivery system will now be generally described with respect to FIGS. 9 and 10. FIG. 9 depicts a side view of the loading tool 520 prior to positioning over a distal end 972 of a delivery system 970, with the loading tool 520 in the open configuration. In this embodiment, the delivery system 970 is configured to deliver the transcatheter valve prosthesis 100 via a transfemoral approach. When configured for transfemoral delivery, the outflow end 103 of the transcatheter valve prosthesis 100 is disposed distal to the inflow end 101 of the transcatheter valve prosthesis 100 within the distal end 972 of the delivery system 970. Further, when configured for transfemoral delivery, the outflow end 103 of the transcatheter valve prosthesis 100 is released and deployed prior to the inflow end 101 of the transcatheter valve prosthesis 100. In this embodiment, the distal end 972 includes a capsule 974 which is configured to constrain the transcatheter valve prosthesis 100 in a radially reduced configuration during delivery in situ.

When a user is preparing to load the transcatheter valve prosthesis 100 into the capsule 974 of the distal end 972 of the delivery system 970, the user will first position the loading tool 520 over the capsule 974 by advancing the splayed opening 562 of the loading tool 520 over the capsule 974. After the loading tool 520 is disposed over the capsule 974, the user transitions the loading tool 520 into the closed configuration. FIG. 10 depicts a side view of the loading tool 520 after positioning over the capsule 974 of the delivery system 970, with the loading tool 520 in the closed configuration. An inner diameter of the hinged body 522 of the loading tool 520 is substantially equal to the outer diameter of the capsule 974 of the delivery system 970. The first and second body portions 524A, 524B that are disposed over the capsule 974 collectively have a tubular configuration when the loading tool 520 is in the closed configuration. With the loading tool 520 in the closed configuration and disposed over the distal end 972, the loading tool 520 is in position for the transcatheter valve prosthesis 100 to be pulled into the capsule 974 of the delivery system 970. The process of loading the transcatheter valve prosthesis 100 into the capsule 974 is described with respect to FIGS. 16 and 17. Further, the hinged body 522 of the loading tool 520 includes several integral features including chamfers, piston ledges, and capsule overhangs for interacting with the delivery system and avoiding damage to the transcatheter valve prosthesis 100 as the transcatheter valve prosthesis 100 is pulled into the delivery system, and these features are described with respect to FIGS. 18 and 19.

FIG. 11 depicts an exploded view of a loading tool 1120 according to another embodiment hereof in which the first and second body portions of the loading tool are attached to each other via adhesive. The loading tool 1120 includes a hinged body 1122 and a collar 1140 slidingly disposed over the hinged body 1122. Similar to the hinged body 522, the hinged body 1122 includes a first body half or portion 1124A and a second body half or portion 1124B. The first and second body halves or portions 1124A, 1124B collectively define the hinged body 1122, which is configured to dynamically open and close mechanically via sliding movement of the collar 1140 similar to the hinged body 522. The hinged body 1122 is sized or configured to be disposed over a distal end of the delivery system during loading of the transcatheter valve prosthesis 100 into a delivery system.

Similar to the loading tool 520, the loading tool 1120 includes resilient clips for locking the collar 1140 and the loading tool 1120 in a closed configuration. Particularly, the first body portion 1124A and the second body portion 1124B includes a resilient clip 1130A, 1130B formed thereon that includes a radial protrusion 1132A, 1132B on an outer surface thereof, respectively. Each resilient clip 1130A, 1130B is a flap or tab formed on its respective body portion such that it is configured to be displaced radially inwards when a pinching force is applied thereto. Each resilient clip 1130A, 1130B includes a first end 1129A, 1129B that is attached to or extends from the respective body portion 1124A, 1124B and a second end 1131A, 1131B that is detached from the respective body portion 1124A, 1124B. The radial protrusions 1132A, 1132B are formed on the second ends 1131A, 1131B of the resilient clips 1130A, 1130B.

Each of the first body portion 1124A and the second body portion 1124B has a first end 1126A, 1126B and a second end 1128A, 1128B, respectively. The first end 1126A of the first body portion 1124A is attached to the first end 1126B of the second body 1124B via adhesive at a joint 1190 and the second end 1128A of the first body portion 1124A is not attached to the second end 1128B of the second body portion 1124B. The attached first ends 1126A, 1126B form a hinged end 1135 of the loading tool 1120. With the first and second body portions 1124A, 1124B being attached via adhesive, the mechanical fastener of the loading tool 520 is omitted. Adjacent to the first ends 1126A, 1126B, each of the first body portion 1124A and the second body portion 1124B includes a semi-circular blunt end such that the semi-circular blunt ends are configured to close one end of the hinged body 1122 when the first and second body portions 1124A, 1124B are joined together. The opposing end of the loading tool 1120 includes a splayed opening 1162, which is similar to splayed opening 562 of the loading tool 520, which allows the loading tool 1120 to easily slide over the delivery system during the loading process, and further to easily slide off the delivery system after the loading process is complete.

Since one end of the hinged body 1122 is closed when the first and second body portions 1124A, 1124B are joined together, the loading tool 1122 is configured for use with a delivery system that is configured to deliver the transcatheter valve prosthesis 100 via a transfemoral approach similar to the loading tool 520 described above with respect to FIGS. 9 and 10.

FIG. 12 depicts an exploded view of a loading tool 1220 according to another embodiment hereof in which the first and second body portions of the loading tool are attached to each other via adhesive, but the loading tool 1220 is open at both ends thereof. The loading tool 1220 includes a hinged body 1222 and a collar 1240 slidingly disposed over the hinged body 1222. Similar to the hinged body 522, the hinged body 1222 includes a first body half or portion 1224A and a second body half or portion 1224B. The first and second body halves or portions 1224A, 1224B collectively define the hinged body 1222, which is configured to dynamically open and close mechanically via sliding movement of the collar 1240 similar to the hinged body 522. The hinged body 1222 is sized or configured to be disposed over a distal end of the delivery system during loading of the transcatheter valve prosthesis 100 into a delivery system.

Similar to the loading tool 1220, the loading tool 1220 includes resilient clips for locking the collar 1240 and the loading tool 1220 in a closed configuration. Particularly, the first body portion 1224A and the second body portion 1224B includes a resilient clip 1230A, 1230B formed thereon that includes a radial protrusion 1232A, 1232B on an outer surface thereof, respectively. Each resilient clip 1230A, 1230B is a flap or tab formed on its respective body portion such that it is configured to be displaced radially inwards when a pinching force is applied thereto. Each resilient clip 1230A, 1230B includes a first end 1229A, 1229B that is attached to or extends from the respective body portion 1224A, 1224B and a second end 1231A, 1231B that is detached from the respective body portion 1224A, 1224B. The radial protrusions 1232A, 1232B are formed on the second ends 1231A, 1231B of the resilient clips 1230A, 1230B.

Each of the first body portion 1224A and the second body portion 1224B has a first end 1226A, 1226B and a second end 1228A, 1228B, respectively. The first end 1226A of the first body portion 1224A is attached to the first end 1226B of the second body 1224B via adhesive at a joint 1290 and the second end 1228A of the first body portion 1224A is not attached to the second end 1228B of the second body portion 1224B. The attached first ends 1226A, 1226B form a hinged end 1235 of the loading tool 1220. The attached first ends 1226A, 1226B may include interlocking or mating surfaces 1238A, 1238B. With the first and second body portions 1224A, 1224B being attached via adhesive, the mechanical fastener of the loading tool 520 is omitted. Adjacent to the first ends 1226A, 1226B, at the hinged end 1235, the loading tool 1220 has a fixed opening 1292. The opposing end of the loading tool 1220 includes a splayed opening 1262, which is similar to splayed opening 562 of the loading tool 520, which allows the loading tool 1220 to easily slide over the delivery system during the loading process, and further to easily slide off the delivery system after the loading process is complete.

Since both ends (i.e., splayed opening 1262 and fixed opening 1292) of the loading tool 1220 are open when the first and second body portions 1224A, 1224B are joined together, the loading tool 1222 may be used with a delivery system configured to deliver the transcatheter valve prosthesis 100 in a transfemoral approach similar to the loading tools 520, 1220 as well as a delivery system configured to deliver the transcatheter valve prosthesis 100 in a transapical approach. The set-up of the loading tool 1220 onto a delivery system configured to deliver the transcatheter valve prosthesis 100 with a transapical approach will now be generally described with respect to FIGS. 13 and 14. FIG. 13 depicts a side view of the loading tool 1220 prior to positioning over a distal end 1372 of a delivery system 1370, with the loading tool 1220 in the open configuration. In this embodiment, the delivery system 1370 is configured to deliver the transcatheter valve prosthesis 100 via a transapical approach. When configured for transapical delivery, the inflow end 101 of the transcatheter valve prosthesis 100 is disposed distal to the outflow end 103 of the transcatheter valve prosthesis 100 within the distal end 1372 of the delivery system 1270. Further, when configured for transapical delivery, the inflow end 101 of the transcatheter valve prosthesis 100 is released and deployed prior to the outflow end 103 of the transcatheter valve prosthesis 100.

When a user is preparing to load the transcatheter valve prosthesis 100 into the distal end 1372 of the delivery system 1370, the user will first position the loading tool 1220 over the distal end 1372 by advancing the fixed opening 1292 at the hinged end 1235 of the loading tool 1220 over the distal end 1372. After the loading tool 1220 is disposed over the distal end 1372, the user transitions the loading tool 1220 into the closed configuration. FIG. 14 depicts a side view of the loading tool 1220 after positioning over the distal end 1372 of the delivery system 1370, with the loading tool 1220 in the closed configuration. An inner diameter of the hinged body 1222 of the loading tool 1220 is substantially equal to the outer diameter of the distal end 1372 of the delivery system 1370. The first and second body portions 1224A, 1224B that are disposed over the distal end 1372 collectively have a tubular configuration when the loading tool 1220 is in the closed configuration. With the loading tool 1220 in the closed configuration and disposed over the distal end 1372, the loading tool 1220 is in position for the transcatheter valve prosthesis 100 to be pulled into the distal end 1372 of the delivery system 1370.

Figure 15A:
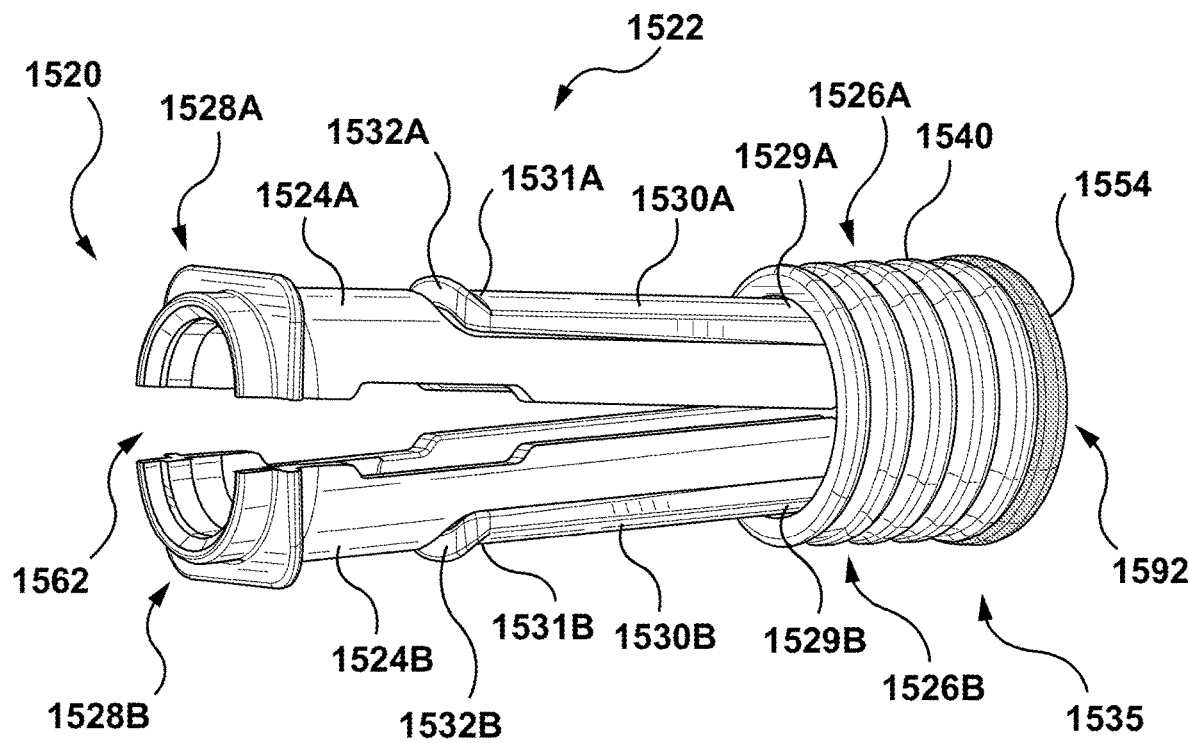
FIG. 15A depicts a perspective view of a loading tool in accordance with another aspect of the disclosure, wherein first and second body portions of the loading tool are mechanically fastened to each other via a ring fastener and the loading tool is open at both ends thereof.
Figure 15B:
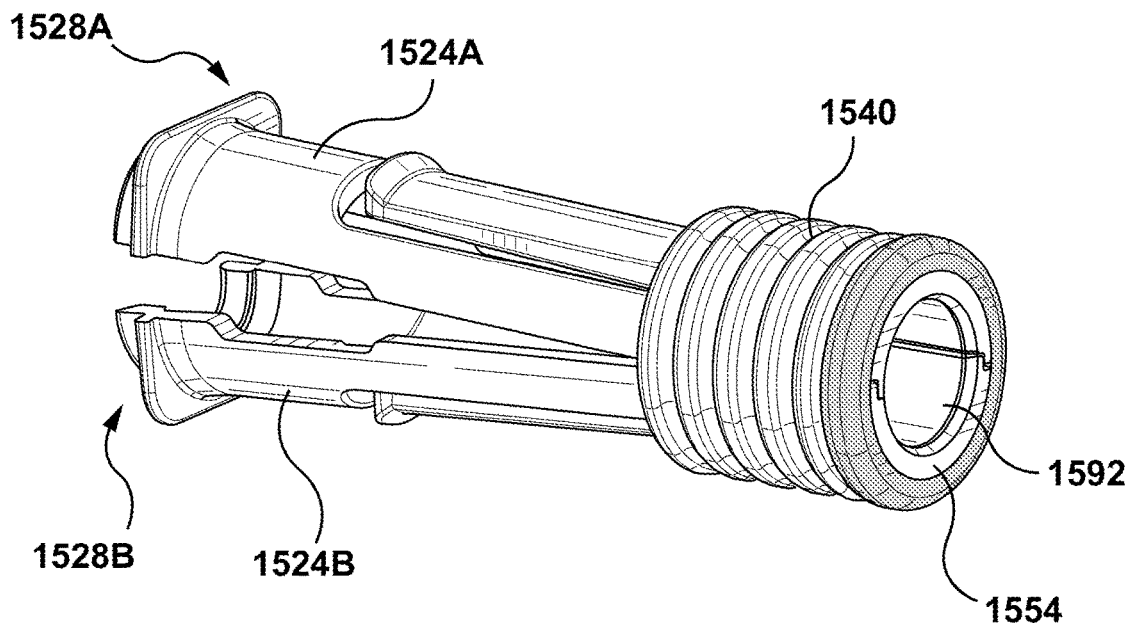
FIG. 15B depicts a different perspective view of the loading tool of FIG. 15A.

FIGS. 15A and 15B depict perspective views of a loading tool 1520 according to another embodiment hereof in which the first and second body portions of the loading tool are attached to each other via an annular or ring fastener such that the loading tool 1520 is open at both ends thereof. The loading tool 1520 includes a hinged body 1522, a collar 1540 slidingly disposed over the hinged body 1522, and a fastener 1554. Similar to the hinged body 522, the hinged body 1522 includes a first body half or portion 1524A and a second body half or portion 1524B. The first and second body halves or portions 1524A, 1524B collectively define the hinged body 1522, which is configured to dynamically open and close mechanically via sliding movement of the collar 1540 similar to the hinged body 522. The hinged body 1522 is sized or configured to be disposed over a distal end of the delivery system during loading of the transcatheter valve prosthesis 100 into a delivery system.

Similar to the loading tool 1520, the loading tool 1520 includes resilient clips for locking the collar 1540 and the loading tool 1520 in a closed configuration. Particularly, the first body portion 1524A and the second body portion 1524B includes a resilient clip 1530A, 1530B formed thereon that includes a radial protrusion 1532A, 1532B on an outer surface thereof, respectively. Each resilient clip 1530A, 1530B is a flap or tab formed on its respective body portion such that it is configured to be displaced radially inwards when a pinching force is applied thereto. Each resilient clip 1530A, 1530B includes a first end 1529A, 1529B that is attached to or extends from the respective body portion 1524A, 1524B and a second end 1531A, 1531B that is detached from the respective body portion 1524A, 1524B. The radial protrusions 1532A, 1532B are formed on the second ends 1531A, 1531B of the resilient clips 1530A, 1530B.

Each of the first body portion 1524A and the second body portion 1524B has a first end 1526A, 1526B and a second end 1528A, 1528B, respectively. The first end 1526A of the first body portion 1524A is attached to the first end 1526B of the second body 1524B via the fastener 1554 and the second end 1528A of the first body portion 1524A is not attached to the second end 1528B of the second body portion 1524B. The attached first ends 1526A, 1526B form a hinged end 1535 of the loading tool 1520.

The fastener 1554 is an annular or ring component that is disposed over the first ends 1526A, 1526B of the loading tool 1520. The fastener 1554 attaches or fastens the first and second body portions 524A, 524B together. The fastener 1544 also contains the collar 1540 so that the collar 1540 cannot slide off the hinged body 1522. Particularly, the fastener 1554 has an outer diameter that is slightly greater than the outer diameter of the collar 1540 so that when the collar 1540 is disposed over the hinged body 1522, the collar 1540 cannot slide over the fastener 1554. Stated another way, the fastener 1554 functions as a stopper for the collar 1540. The loading tool 1520 is thus provided to the user as a single, assembled tool that does not require any assembly by the user.

Adjacent to the first ends 1526A, 1526B, adjacent to the hinged end 1535, the loading tool 1520 has a fixed opening 1592. The opposing end of the loading tool 1520 includes a splayed opening 1562, which is similar to splayed opening 562 of the loading tool 1520, which allows the loading tool 1520 to easily slide over the delivery system during the loading process, and further to easily slide off the delivery system after the loading process is complete.

Since both ends (i.e., splayed opening 1562 and fixed opening 1592) of the loading tool 1520 are open when the first and second body portions 1524A, 1524B are joined together, the loading tool 1522 may be used with a delivery system configured to deliver the transcatheter valve prosthesis 100 in either a transfemoral approach similar to the loading tool 1520 described above with respect to FIGS. 9 and 10 as well as a transapical approach similar to the loading tool 1220 described above with respect to FIGS. 13 and 14.

Referring now to FIGS. 16-19, a method of loading a self-expanding prosthesis into a delivery system will be described. For sake of illustration, use of the loading tool is described herein with respect to loading the transcatheter valve prosthesis 100 which is configured for implantation within a native mitral valve, as the structure of the transcatheter valve prosthesis 100 has already been described in detail above. However, as previously stated, the loading tools described herein may be utilized when loading any self-expanding prosthesis into a delivery system, and it is not required that the self-expanding prosthesis include a prosthetic valve component disposed therein. Further, for sake of illustration, use of the loading tool is described herein with respect to loading the transcatheter valve prosthesis 100 onto a delivery system 1670 having a distal end 1672. In this embodiment, the distal end 1672 includes a capsule 1674 which is configured to constrain the transcatheter valve prosthesis 100 in a radially reduced configuration during delivery in situ and includes a piston 1680 for hydraulic actuation of the capsule 1672. The delivery system 1670 is described in FIGS. 54A-55C of U.S. Pat. No. 9,034,032 to McLean et al. and International Patent Application Ser. No. PCT/US2014/029549 to McLean et al., previously incorporated by reference in its entirety.

The transcatheter valve prosthesis 100 is first be crimped down to a reduced diameter by advancing the transcatheter valve prosthesis 100 into a loading cone or funnel 1676. In another embodiment (not shown), the transcatheter valve prosthesis 100 may be crimped down to a reduced diameter via a radial crimper. The loading funnel 1676 is a conical or tapered component that includes a first end 1675 having a first diameter and a second end 1677 having a second diameter that is less than the first diameter. The transcatheter valve prosthesis 100 in its expanded or shape set configuration is positioned into the first end 1675 of the loading funnel 1676 and advanced through the loading funnel 1676 towards the second end 1677 thereof to reduce its diameter. With the transcatheter valve prosthesis 100 disposed therein, the assembly of the loading funnel 1676 and the transcatheter valve prosthesis 100 disposed therein is placed over an inner shaft 1678 of a delivery system 1670 in a saline bath. The assembly of the loading funnel 1676 and the transcatheter valve prosthesis 100 is positioned proximal to a proximal end of the capsule 1674. The transcatheter valve prosthesis 100 is advanced through the loading funnel 1676 until attachment bars 105 of the transcatheter valve prosthesis 100 extend or protrude from the second end 1677 of the loading funnel 1676. The attachment bars 105 are releasably coupled to the piston 1680 of the delivery system 1670. For example, the transcatheter valve prosthesis 100 may be releasably coupled to the piston 1680 by, for example, corresponding or mating slots (not shown) formed on a tubular shaft of the piston that is slidably mounted over the inner shaft 1678, the slots being configured to receive the attachment bars 105.

At this stage or point of the method of loading, which is illustrated in the side view of FIG. 16, the loading tool 520 may be positioned over the capsule 1674 of the delivery system 1670. The delivery system 1670 is still located within the saline bath, and the assembly of the loading funnel 1676 and the transcatheter valve prosthesis 100 is positioned proximal to a proximal end of the capsule 1674 as described above. FIG. 16 depicts a side view of the loading tool 520 prior to positioning over the capsule 1674 of the delivery system 1670, with the loading tool 520 in its open configuration. As described herein, when in the open configuration, the second end 528A of the first body portion 524A and the second end 528B of the second body portion 524B are radially spaced apart from each other and the collar 540 is disposed over the first ends 526A, 526B of the first and second body portions 524A, 524B.

While in the open configuration, the loading tool 520 is positioned or placed over the capsule 1674 of the delivery system 1670 and while the loading tool 520 is disposed over the capsule 1674 of the delivery system 1670, the collar 540 is slid over the hinged body 522 until the loading tool 520 is in a closed configuration. As described herein, when in the closed configuration, the second end 528A of the first body portion 524A and the second end 528B of the second body portion 524B are disposed directly adjacent to each other and the collar 540 is disposed over the second ends 528A, 528B of the first and second body portions 524A, 524B, and the radial protrusions 532A, 532B abut against the collar 540 to lock the loading tool 520 in the closed configuration. FIG. 17 depicts a side view of the loading tool 520 after transitioning the loading tool 520 to its closed configuration.

Figure 18:
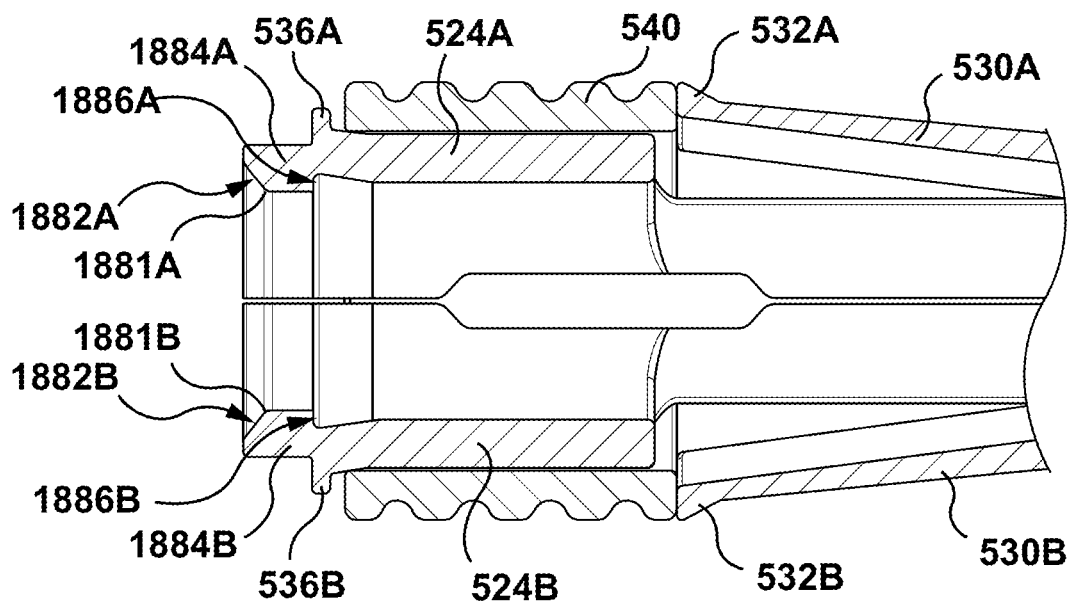
FIG. 18 depicts a sectional side view of a portion of the loading tool of FIG. 5, wherein the loading tool is in the closed configuration.
Figure 19:
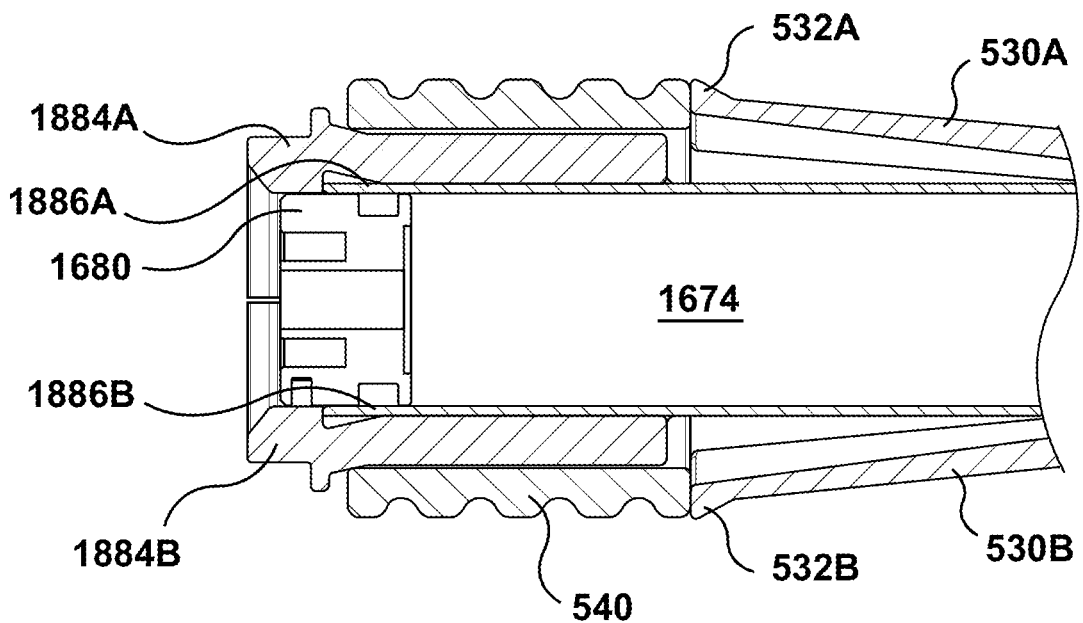
FIG. 19 depicts the sectional side view of FIG. 18 with a capsule and a piston of the delivery system of FIG. 17 disposed therein.

The loading tool 520 includes several features for interacting with the delivery system 1670 and avoiding damage to the transcatheter valve prosthesis 100 as the transcatheter valve prosthesis 100 is pulled into the delivery system 1670. More particularly, such features are best shown in FIGS. 18 and 19. FIG. 18 depicts a sectional side view of a portion of the loading tool 520 in the closed configuration, while FIG. 19 depicts the same sectional side view with the capsule 1674 and the piston 1680 disposed within the loading tool 520. Each of the first and second body portions 524A, 524B of the loading tool 520 includes a chamfer or transitional leading edge 1882A, 1882B on an inner surface 1881A, 1881B thereof at the second ends 528A, 528B thereof. The chamfers 1882A, 1882B provide a smooth transition between the loading funnel 1676 and the capsule 1674, and thus help to avoid damage to the transcatheter valve prosthesis 100 as it is pulled into the capsule 1674.

In addition, with continued reference to FIGS. 18 and 19, each of the first and second body portions 524A, 524B of the loading tool 520 includes a piston ledge 1884A, 1884B at the second ends 528A, 528B thereof. The piston ledges 1884A, 1884B extend beyond the flanges 536A, 536B. During use, the piston ledges 1884A, 1884B initially extend over the connection between the attachment bars 105 and the piston 1680 of the delivery system 1670, which are releasably attached together. The piston ledges 1884A, 1884B form a ring gauge around the piston 1680 and help to retain the attachment bars 105 in place during loading, as undesired movement of the attachment bars 105 may cause mis-loading and/or damage to the transcatheter valve prosthesis 100 and/or the delivery system 1670.

In addition, with continued reference to FIGS. 18 and 19, each of the first and second body portions 524A, 524B of the loading tool 520 includes a capsule overhang 1886A, 1886B formed on the inner surfaces 1881A, 1881B thereof at the second ends 528A, 528B thereof. The capsule overhangs 1886A, 1886B are integral stepped edges that are configured to grip or cover the proximal edge of the capsule 1674, thereby preventing direct contact between the transcatheter valve prosthesis 100 and the proximal end of the capsule 1674 when the transcatheter valve prosthesis 100 is pulled into the capsule 1674. The transcatheter valve prosthesis 100 may inadvertently be damaged by friction and/or direct contact with the capsule 1674 during loading, so the capsule overhangs 1886A, 1886B help to avoid damage to the transcatheter valve prosthesis 100 as it is pulled into the capsule 1674. In addition, the capsule overhangs 1886A, 1886B are configured to retain the attachment bars 105 in place during loading to ensure that the attachment bars 105 do not dislodge or pop out after loading, as undesired movement of the attachment bars 105 may cause mis-loading and/or damage to the transcatheter valve prosthesis 100 and/or the delivery system 1670.

After the loading tool 520 is positioned over the capsule 1674 as shown in FIG. 17, the transcatheter valve prosthesis 100 is pulled into the capsule 1674 via movement of the piston 1680. Stated another way, the piston 1680 pulls or retracts the transcatheter valve prosthesis 100 into the delivery system 1670. While the transcatheter valve prosthesis 100 is being pulled into the delivery system 1670, the loading tool 520 remains locked in its closed configuration over the capsule 1674 via the resilient clips 530A, 530B of the loading tool 520. The loading tool 520 being locked in the closed configuration ensures that the transcatheter valve prosthesis 100 is protected from mis-load related damage during loading.

After the transcatheter valve prosthesis 100 is loaded into the distal end 1672 of the delivery system 1670, the loading tool 520 is removed from the delivery system 1672. The loading tool 520 may be removed when a pinching force is applied to displace the resilient clips 530A, 530B radially inward as described herein. The collar 540 is slid over the hinged body 522 while the resilient clips 530A, 530B are displaced radially inward until the loading tool 520 reverts to its open configuration. Once in the open configuration, the loading tool 520 is removed from the distal end 1672 of the delivery system 1670.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A loading tool to facilitate loading a self-expanding prosthesis into a delivery system, the loading tool comprising:
    a hinged body including a first body portion and a second body portion, each of the first body portion and the second body portion having a first end and a second end, wherein the first end of the first body portion is attached to the first end of the second body and the second end of the first body portion is not attached to the second end of the second body portion, and wherein each of the first body portion and the second body portion includes a resilient clip formed thereon that includes a radial protrusion on an outer surface thereof, each resilient clip being configured to be displaced radially inwards when a pinching force is applied thereto; and
    a collar slidingly disposed over the hinged body, wherein the loading tool has an open configuration in which the second end of the first body portion and the second end of the second body portion are radially spaced apart from each other and the collar is disposed over the first ends of the first and second body portions, and wherein the loading tool has a closed configuration in which the second end of the first body portion and the second end of the second body portion are disposed directly adjacent to each other and the collar is disposed over the second ends of the first and second body portions, and wherein the radial protrusions are configured to lock the loading tool in the closed configuration when the resilient clips are not displaced radially inwards.

2. The loading tool of claim 1, wherein each of the first body portion and the second body portion has a flange on an outer surface thereof at the second end thereof and wherein the collar is sandwiched between the flanges and the radial protrusions on the resilient clips when the collar locks the hinged body in the closed configuration.

3. The loading tool of claim 2, wherein each flange has a square profile.

4. The loading tool of claim 1, wherein each radial protrusion has a tapered outer surface that permits the collar to slide in a direction from the first ends of the first and second body portions towards the second ends of the first and second body portions and wherein each radial protrusion has an end surface that does not permit the collar to slide in a direction from the second ends of the first and second body portions towards the first ends of the first and second body portions unless the resilient clips are displaced radially inwards by the pinching force.

5. The loading tool of claim 1, wherein the loading tool is prevented from opening when the radial protrusions lock the loading tool in the closed configuration.

6. The loading tool of claim 5, wherein the resilient clips are configured to be displaced radially inwards to release the collar.

7. The loading tool of claim 1, wherein the hinged body is configured to be disposed over a distal end of the delivery system during loading of the self-expanding prosthesis into the delivery system.

8. The loading tool of claim 7, wherein the hinged body is configured to be disposed over a capsule of the delivery system when the self-expanding prosthesis is positioned into the capsule.

9. The loading tool of claim 8, wherein the second ends of the first and second body portions each include a stepped edge formed on an inner surface thereof configured to prevent the self-expanding prosthesis from contacting a first end of the capsule when the self-expanding prosthesis is positioned into the capsule and configured to retain attachment bars of the self-expanding prosthesis.

10. The loading tool of claim 1, wherein the first and second body portions collectively have a tubular configuration when the loading tool is in the closed configuration.

11. A method of loading a self-expanding prosthesis into a delivery system, the method comprising:
placing a loading tool in an open configuration, the loading tool including a hinged body and a collar slidingly disposed over the hinged body, the hinged body including a first body portion and a second body portion, each of the first body portion and the second body portion having a first end and a second end, wherein the first end of the first body portion is attached to the first end of the second body and the second end of the first body portion is not attached to the second end of the second body portion, and wherein each of the first body portion and the second body portion includes a resilient clip formed thereon that includes a radial protrusion on an outer surface thereof, each resilient clip being configured to be displaced radially inwards when a pinching force is applied thereto, wherein in the open configuration the second end of the first body portion and the second end of the second body portion are radially spaced apart from each other and the collar is disposed over the first ends of the first and second body portions, and
disposing the loading tool in the open configuration over a distal end of the delivery system;
while the loading tool is disposed over a distal end of the delivery system, sliding the collar over the hinged body until the loading tool is in a closed configuration, wherein in the closed configuration the second end of the first body portion and the second end of the second body portion are disposed directly adjacent to each other and the collar is disposed over the second ends of the first and second body portions, and wherein the radial protrusions lock the loading tool in the closed configuration when the resilient clips are not displaced radially inwards; and
loading the self-expanding prosthesis into the distal end of the delivery system while the radial protrusions lock the loading tool in the closed configuration.

12. The method of claim 11, further comprising:
after the self-expanding prosthesis is loaded into the distal end of the delivery system, applying a pinching force to displace the resilient clips radially inward;
sliding the collar over the hinged body while the resilient clips are displaced radially inward until the loading tool is in the open configuration; and
removing the loading tool from the distal end of the delivery system.

13. The method of claim 11, wherein the self-expanding prosthesis is a mitral valve prosthesis.

14. The method of claim 11, wherein each of the first body portion and the second body portion has a flange on an outer surface thereof at the second end thereof and wherein the collar is sandwiched between the flanges and the radial protrusions on the resilient clips when the collar locks the hinged body in the closed configuration.

15. The method of claim 14, wherein each flange has a square profile and the flange sets against a flat surface during the step of loading the self-expanding prosthesis.

16. The method of claim 11, wherein each radial protrusion has a tapered outer surface that permits the collar to slide in a direction from the first ends of the first and second body portions towards the second ends of the first and second body portions and wherein each radial protrusion has an end surface that does not permit the collar to slide in a direction from the second ends of the first and second body portions towards the first ends of the first and second body portions unless the resilient clips are displaced radially inwards by the pinching force.

17. The method of claim 11, wherein the loading tool is prevented from opening to the open configuration when the radial protrusions lock the loading tool in the closed configuration.

18. The method of claim 11, wherein the distal end of the delivery system is a capsule.

19. The method of claim 18, wherein the second ends of the first and second body portions each include a stepped edge formed on an inner surface thereof configured to prevent the self-expanding prosthesis from contacting a first end of the capsule when the self-expanding prosthesis is positioned into the capsule and configured to retain attachment bars of the self-expanding prosthesis.

20. The method of claim 11, wherein the first and second body portions collectively have a tubular configuration when the loading tool is in the closed configuration.

* * * * *